US006822079B2

(12) United States Patent  
Coruzzi et al.

(10) Patent No.: US 6,822,079 B2  
(45) Date of Patent: Nov. 23, 2004

(54) PLANT NITROGEN REGULATORY P-PII POLYPEPTIDES

(75) Inventors: Gloria M. Coruzzi, New York, NY (US); Hon-Ming Lam, Hong Kong (HK); Ming-Hsiun Hsieh, Woodside, NY (US)

(73) Assignee: New York University, New York, NY (US)

(*) Notice: Subject to any disclaimer, the term of this patent is extended or adjusted under 35 U.S.C. 154(b) by 465 days.

(21) Appl. No.: 09/756,541

(22) Filed: Jan. 8, 2001

(65) Prior Publication Data

US 2004/0002053 A1 Jan. 1, 2004

Related U.S. Application Data

(63) Continuation of application No. 08/899,330, filed on Jul. 23, 1997, now Pat. No. 6,177,275.

(51) Int. Cl.$^7$ ......................... C07K 14/415; C07K 4/10; C07K 19/00

(52) U.S. Cl. ....................... 530/370; 530/300; 530/324; 530/325; 530/326; 530/327; 530/328; 530/329; 530/330; 530/350

(58) Field of Search .............................. 530/300, 324, 530/325, 326, 327, 328, 329, 330, 350, 370

(56) References Cited

PUBLICATIONS

Colonna–Romano et al., 1987, "Tight linkage of glnA and a putative regulatory gene in Rhizobium leguminosarum", Nucleic Acids Res. 15:1951–1964.

de Zamaroczy et al., 1990, "Characterization of three different nitrogen–regulated promoter regions for the expression of glnB and glnA in *Azospirillum brasilense*", Mol. Gen. Genet. 224:421–430.

Edwards & Coruzzi, 1989, "Photorespiration and light act in concert to regulate the expression of the nuclear gene for chloroplast glutamine synthetase", Plant Cell 1:241–248.

Faure et al., 1994, "Zea3: A pleiotropic mutation affecting cotyledon development, cytokinin resistance and carbon–nitrogen metabolism", Plant J. 5:481–491.

Foor et al., 1975, "Regulation of synthesis of glutamine synthetase by adenylylated glutamine synthetase", Proc. Natl. Acad. Sci. USA 72:4844–4848.

Forchhammer & De Marsac, 1994, "The PII protein in the cyanobacterium Synechococcus sp. strain PCC 7942 is modified by serine phosphorylation and signals the cellular N–status", J. Bacteriol. 176:84–91.

Holtel & Merrick, 1988, "Identification of the *Klebsiella pneumoniae* glnB gene: Nucleotide sequence of wild–type and mutant alleles", Mol. Gen. Genet. 215:134–138.

Kranz et al., 1990, "Inactivation, sequence, and lacZ fusion analysis of a regulatory locus required for repression of nitrogen fixation genes in *Rhodobacter capsulatus*", J. Bacteriol. 172:53–62.

Lam et al., 1994, "Metabolic regulation of the gene encoding glutamine dependent asparagine synthetase in *Arabidopsis thaliana*", Plant Physiol. 106:1347–1357.

B. Magasanik, 1988, "Reversible phosphorylation of an enhancer binding protein regulates the transcription of bacterial nitrogen utilization genes", TIBS 13:475–479.

B. Magasanik, 1993, "The regulation of nitrogen utilization in enteric bacteria", J. Cell. Biochem. 51:34–40.

Martin et al., 1989, "*Bradyrhizobium japonicum* glnB, a putative nitrogen–regulatory gene, is regulated by NtrC at tandem promoters", J. Bacteriol. 171:5638–5645.

Ninfa & Magasanik, 1986, "Covalent modification of the glnG product, NRI, by the glnL product, NRII, regulates the transcription of the glnALG operon in *Escherichia coli*", Proc. Natl. Acad. Sci. USA 83:5909–5913.

Son & Rhee, 1987, "Cascade control of *Escherichia coli* glutamine synthetase", J. Biol. Chem. 262:8690–8695.

Souillard & Sibold, 1989, "Primary structure, functional organization and expression of nitrogenase structural genes of the thermophilic archaebacterium *Methanococcus thermolithotrophicus*", Mol. Microbiol. 3:541–551.

Stam et al., 1997, The Silence of Genes in Transgenic Plants, Annals of Botany 79:3–12.

C. Stewart, 1993, "The powers and pitfalls of parsimony", Nature 361: 603–607.

Tsinoremas et al., 1991, "Photosynthetic electron transport controls nitrogen assimilation in cyanobacteria by means of posttranslational modification of the glnB gene product", Proc. Natl. Acad. Sci. USA 88:4565–4569.

(List continued on next page.)

Primary Examiner—Terry McKelvey  
(74) Attorney, Agent, or Firm—Jones Day

(57) ABSTRACT

The present invention generally relates to plant nitrogen regulatory PII gene (hereinafter P-PII gene), a gene involved in regulating plant nitrogen metabolism. The invention provides P-PII nucleotide sequences, expression constructs comprising said nucleotide sequences, and host cells and plants having said constructs and, optionally expressing the P-PII gene from said constructs. The invention also provides substantially pure P-PII proteins.

Figure 1B:
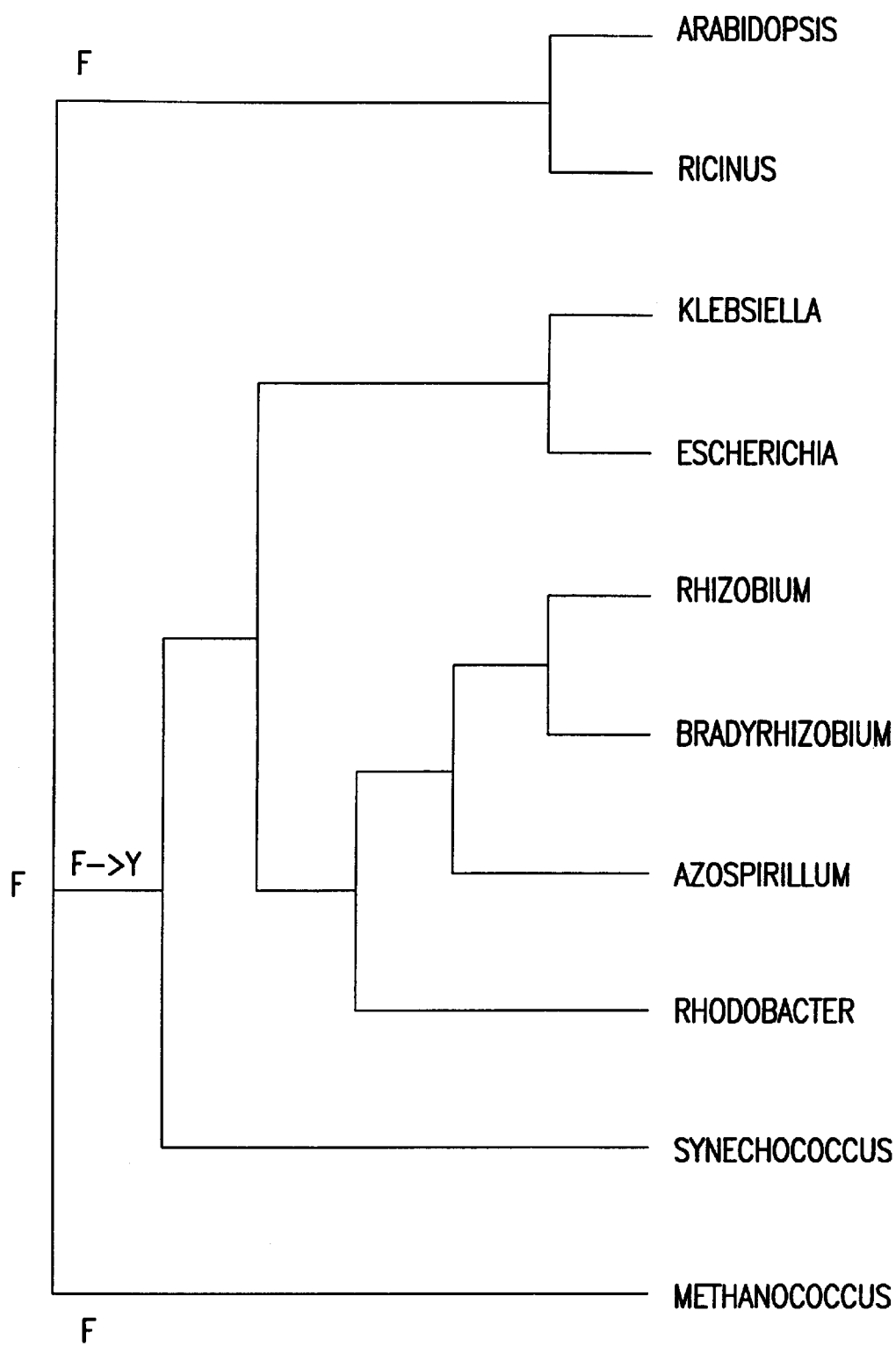

The P-PII nucleotide sequences and constructs of the invention may be used to engineer organisms to overexpress wild-type or mutant P-PII regulatory protein. Engineered plants that overexpress or underexpress P-PII regulatory protein may have increased nitrogen assimilation capacity. Engineered organisms may be used to produce P-PII proteins which, in turn, can be used for a variety of purposes including in vitro screening of herbicides. P-PII nucleotide sequences have additional uses as probes for isolating additional genomic clones having the promoters of P-PII gene. P-PII promoters are light- and/or sucrose-inducible and may be advantageously used in genetic engineering of plants.

10 Claims, 13 Drawing Sheets

PUBLICATIONS van de Loo et al., 1995, "Expressed sequence tags from developing castor seeds", Plant Physiol. 108:1141–1150.

van Heeswijk et al., 1993, "The genes of the glutamine synthetase adenylylation cascade are not regulated by nitrogen in *Escherichia coli*", Mol. Microbiol. 9:443–457.

Vincentz et al., 1993, "Regulation of nitrate and nitrite reductase expression in *Nicotiana plumbaginifolia* leaves by nitrogen and carbon metabolites", Plant J. 3:315–324.

Wray et al., 1994, "The nitrogen–regulated *Bacillus subtilis* nrgAB operon encodes a membrane protein and a protein highly similar to the *Escherichia coli* glnB–encoded PII protein", J. Bacteriol. 176:108–114.

```
                  *******    *   *  **     ** ****  * *****  **
Plant       At    FYKVEAIVRP WRIQQNSSAL LKIGIRGVTV SDVRGFGAQG
            Ric   FYKVEAILRP WRVSQNSSAL LKIGIRGVTV SDVRGFGAQG
            Kp    MKKIDAIIKP FKLDDVREAL AEVGITGMTV TEVKGFGRQK
            Ec    MKKIDAIIKP FKLDDVREAL AEVGITGMTV TEVKGFGRQK
            RL    MKKIEAIIKP FKLDEVR-SP SGVGLQGITV TEAKGFGRQK
Bacteria    Bj    MKKIEAIIKP FKLDEVR-SL SGVGLQGITV TEAKGFGRQK
            Az    MKKIEAIIKP FKLDEVKEAL HEVGIKGITV TEAKGFGRQK
            Rc    MKKVEAIIKP FKLDDVKEAL QEAGIQGLSV IEVKGFGRQK
            Sy    MKKIEAIIRP FKLDEVKIAL VNAGIVGMTV SEVRGFGRQK Archaebacteria Mt1 MKMIKAIVRP DKVDDIVDSL ENAGYPAFTK INSVGRGKDG
               Mt2 MKEVIAIIRP NTVSKTVKAL DVVGFPAVTM AECFGRGKQK
                 1
                      ↓            ↓
                 * ***  ***  *   *  **  * ****   **  ** ** ***
Plant       At    GSIERHGGSE FSEDKFVAKV KMEIVVKKDQ VESVINTIIE
            Ric   GSIERQGGSE FSEDKFVAKV KMEIVVSKDQ VEDVIEKIIE
            Kp    GHTELYRGAE YMVD-FLPKV KIEIVVTDDI VDTCVDTIIR
            Ec    GHTELYRGAE YMVD-FLPKV KIEIVVPDDI VDTCVDTIIR
            RL    GHTELYRGAE YVVD-FLPKV KVEVVLADEN AEAVIEAIRK
Bacteria    Bj    GHTDLYTGAE YIVD-FLPKV KIEIVIGDDL VERAIDAIRR
            Az    GHTELYRGAE YVVD-FLPKV KIEVVMEDSL VERAIEAIQQ
            Rc    GHTELYRGAE YVVD-FLPKV KIEMVLPDEM VDIAIEAIVG
            Sy    GQIERYRGSE YTVE-FLQKL KLEIVVEDAQ VDTVIDKIVA Archaebacteria Mt1 GLKVGE---I FY-D-ELPKT ILLIAVNDDE VDEVVGLIKS
               Mt2 GYEEGEKEGR FIK--YIPKR LISIVVDDAD VPLVVGIISK
                  ^          51
                          []
                  *********  *******   *  ******   **      *
Plant       At    GARTGEIGDG KIFVLPVSDV IRVRTGERGE KAE
            Ric   EARTGEIGDG KIFLLPVSDV IRVRTGERGD KAE
            Kp    TACTGKIGDG KIFVFDVARV IRIRTGEEDD AAI
            Ec    TACTGKIGDG KIFVFDVARV IRIRTGEEDD AAI
            RL    AACTGRIGDG KIFVSNVEEV IRIRTGETGI DAI
Bacteria    Bj    AACTGRIGDG KIFVSNIEEA IRIRTGESGL DAI
            Az    AAHTGRIGDG KIFVTPVEEV VRIRTGEKGG DAI
            Rc    AARTEKIGDG KIFVSSIEQA IRIRTGETGE DAV
            Sy    AARTGEIGDG KIFVSPVDQT IRIRTGEKNA DAI Archaebacteria Mt1 SASTGNFGDG KIFIQPITEA YTIRTGETGI ---
               Mt2 VNRTGSFGDG RIFVLPVEEA IRVRTGETGE IAI
                                                     112
```

FIG. 1A

```
  1  ctgaaagttg tgttaaaaaa aaaactagaa tcatggcggc gtcaatgacg
 51  aaacccatct caataacttc tctcggtttc tattctgatc gaaagaacat
101  tgctttctct gattgcattt cgatttgttc tggattcaga cattcccgac
151  catcttgcct cgatttggtc acaaagtcac cgagtaataa cagtcgtgtt
201  ttacctgtcg ttagtgccca aatatcttct gattatattc cagactcgaa
251  attttacaag gtggaagcaa ttgtcagacc atggagaatc cagcaagttt
301  catcggcttt actgaaaatc gggattcgag gtgttactgt ttctgatgtg
351  agagggtttg gtgcacaagg aggttctacc gagagacacg gtggctctga
401  gttctcggaa gacaaatttg ttgctaaagt taagatggaa atcgttgtta
451  agaaagacca agtggaatct gtaatcaaca caataattga aggagcaagg
501  acaggagaga ttggtgatgg caagattttt gttttgcctg tgtcagatgt
551  cataagagtt aggacaggtg agcgtgggga gaaagcagag aagatgactg
601  gtgatatgct ttcaccgtct taggaacaaa cagagctcaa gaatggtttt
651  ttttttttc atttcggtct ctagattctg cgaataataa tgaatggagt
701  ctgtgtttgg tttcatgttg aatcgatcaa gatgtgtttt taactgtaca
751  tgaattatgc agaaacatct gtcctggttc tcagacatcg aaactctgtt
801  cctaataaaa aaaaaaa
```

FIG. 12

```
  1  GCGGTGTCGG CCGCTCTAGA ACTAGTGGAT CCCCCGGGCT GCAGGAATTC
 51  GGCACGAGGC TACTGCGAAA CTGGGCTTGC TCACTCCTCT TCATTCTAAT
101  AACATCAAGA AAGAATTCCC TGTTTTTGAT TTCAGTTTGT TTTGTCCAGA
151  GCTTAGACAT TCTCGGTTTT CTCACTTTAA CACCGCGGTC AAGCGCGTAA
201  GATATGCCCC CGTCGTTCCT GTGATTAATG CCCAAAGCTC GCCTGACTAC
251  ATTCCTGATG CTAAATTCTA CAAAGTGGAA GCAATTCTCA GGCCCTGGCG
301  AGTCTCGCAA GTTTCCTCGG CTTTGCTAAA AATTGGTATT CGAGGTGTTA
351  CTGTTTCTGA TGTTCGAGGT TTTGGTGCTC AAGGTGGTTC AACTGAGAGG
401  CAGGGCGGCT CAGAATTTTC TGAAGACAAG TTTGTTGCTA AAGTTAAGAT
451  GGAGATCGTG GTTAGCAAAG ACCAGGTTGA GGATGTTATA GAAAAAATCA
501  TTGAGGAGGC AAGAACTGGA GAGATTGGAG ACGGCAAGAT TTTCTTGCTG
551  CCTGTTTCAG ATGTAATAAG AGTCCGCACT GGTGAGCGGG GTGATAAGGC
601  TGAGAGGATG ACAGGAGGGC GATCTGACAT GAGTACTTCT GCTTGACTGC
651  TGTGACCAGC AATATAGCAT TCAGGACTAA CTGTCCTTTG AGAAAGCCCC
701  GCCCTTATTA GCCATTATCC AGTATAGCTT GATAATTTGA ATTTTTTGTT
751  TTCTTAACTA AAGAAACAAA GATCTTTTCA TTATCCTGTT GATGATAATT
801  GAAAACGGAA GGATCGCGAA TTTGTTCAAG TGCTTGCAAG ATAAATAACA
851  AGAAGAGGAG TAATGTTAAC AAAAAAAAAA AAAAAAAAAA ACTCGAG
```

FIG.13

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 113 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Phe Tyr Lys Val Glu Ala Ile Val Arg Pro Trp Arg Ile Gln Gln Val
 1               5                  10                  15

Ser Ser Ala Leu Leu Lys Ile Gly Ile Arg Gly Val Thr Val Ser Asp
            20                  25                  30

Val Arg Gly Phe Gly Ala Gln Gly Gly Ser Thr Glu Arg His Gly Gly
            35                  40                  45

Ser Glu Phe Ser Glu Asp Lys Phe Val Ala Lys Val Lys Met Glu Ile
        50                  55                  60

Val Val Lys Lys Asp Gln Val Glu Ser Val Ile Asn Thr Ile Ile Glu
65                  70                  75                  80

Gly Ala Arg Thr Gly Glu Ile Gly Asp Gly Lys Ile Phe Val Leu Pro
                85                  90                  95

Val Ser Asp Val Ile Arg Val Arg Thr Gly Glu Arg Gly Glu Lys Ala
            100                 105                 110

Glu
```

(2) INFORMATION FOR SEQ ID NO: 2:

(i) SEQUENCE CHARACTERISTICS:
      (A) LENGTH: 113 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 2:

```
Phe Tyr Lys Val Glu Ala Ile Leu Arg Pro Trp Arg Val Ser Gln Val
 1               5                  10                  15

Ser Ser Ala Leu Leu Lys Ile Gly Ile Arg Gly Val Thr Val Ser Asp
            20                  25                  30

Val Arg Gly Phe Gly Ala Gln Gly Gly Ser Thr Glu Arg Gln Gly Gly
            35                  40                  45

Ser Glu Phe Ser Glu Asp Lys Phe Val Ala Lys Val Lys Met Glu Ile
        50                  55                  60

Val Val Ser Lys Asp Gln Val Glu Asp Val Ile Glu Lys Ile Ile Glu
65                  70                  75                  80

Glu Ala Arg Thr Gly Glu Ile Gly Asp Gly Lys Ile Phe Leu Leu Pro
                85                  90                  95

Val Ser Asp Val Ile Arg Val Arg Thr Gly Glu Arg Gly Asp Lys Ala
            100                 105                 110

Glu
```

(2) INFORMATION FOR SEQ ID NO: 3:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

```
Met Lys Lys Ile Asp Ala Ile Ile Lys Pro Phe Lys Leu Asp Asp Val
  1               5                  10                  15

Arg Glu Ala Leu Ala Glu Val Gly Ile Thr Gly Met Thr Val Thr Glu
             20                  25                  30

Val Lys Gly Phe Gly Arg Gln Lys Gly His Thr Glu Leu Tyr Arg Gly
         35                  40                  45

Ala Glu Tyr Met Val Asp Phe Leu Pro Lys Val Lys Ile Glu Ile Val
     50                  55                  60

Val Thr Asp Asp Ile Val Asp Thr Cys Val Asp Thr Ile Ile Arg Thr
 65                  70                  75                  80

Ala Gln Thr Gly Lys Ile Gly Asp Gly Lys Ile Phe Val Phe Asp Val
                 85                  90                  95

Ala Arg Val Ile Arg Ile Arg Thr Gly Glu Glu Asp Asp Ala Ala Ile
                100                 105                 110
```

(2) INFORMATION FOR SEQ ID NO: 4:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Met Lys Lys Ile Asp Ala Ile Ile Lys Pro Phe Lys Leu Asp Asp Val
  1               5                  10                  15

Arg Glu Ala Leu Ala Glu Val Gly Ile Thr Gly Met Thr Val Thr Glu
             20                  25                  30

Val Lys Gly Phe Gly Arg Gln Lys Gly His Thr Glu Leu Tyr Arg Gly
         35                  40                  45

Ala Glu Tyr Met Val Asp Phe Leu Pro Lys Val Lys Ile Glu Ile Val
     50                  55                  60

Val Pro Asp Asp Ile Val Asp Thr Cys Val Asp Thr Ile Ile Arg Thr
 65                  70                  75                  80

Ala Gln Thr Gly Lys Ile Gly Asp Gly Lys Ile Phe Val Phe Asp Val
                 85                  90                  95

Ala Arg Val Ile Arg Ile Arg Thr Gly Glu Glu Asp Asp Ala Ala Ile
                100                 105                 110
```

(2) INFORMATION FOR SEQ ID NO: 5:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

Met Lys Lys Ile Glu Ala Ile Ile Lys Pro Phe Lys Leu Asp Glu Val
1               5                   10                  15

Arg Ser Pro Ser Gly Val Gly Leu Gln Gly Ile Thr Val Thr Glu Ala
            20                  25                  30

Lys Gly Phe Gly Arg Gln Lys Gly His Thr Glu Leu Tyr Arg Gly Ala
        35                  40                  45

Glu Tyr Val Val Asp Phe Leu Pro Lys Val Lys Val Glu Val Val Leu
    50                  55                  60

Ala Asp Glu Asn Ala Glu Ala Val Ile Glu Ala Ile Arg Lys Ala Ala
65                  70                  75                  80

Gln Thr Gly Arg Ile Gly Asp Gly Lys Ile Phe Val Ser Asn Val Glu
                85                  90                  95

Glu Val Ile Arg Ile Arg Thr Gly Glu Thr Gly Ile Asp Ala Ile
            100                 105                 110

(2) INFORMATION FOR SEQ ID NO: 6:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

Met Lys Lys Ile Glu Ala Ile Ile Lys Pro Phe Lys Leu Asp Glu Val
1               5                   10                  15

Arg Ser Leu Ser Gly Val Gly Leu Gln Gly Ile Thr Val Thr Glu Ala
            20                  25                  30

Lys Gly Phe Gly Arg Gln Lys Gly His Thr Asp Leu Tyr Arg Gly Ala
        35                  40                  45

Glu Tyr Ile Val Asp Phe Leu Pro Lys Val Lys Ile Glu Ile Val Ile
    50                  55                  60

Gly Asp Asp Leu Val Glu Arg Ala Ile Asp Ile Arg Arg Ala Ala
65                  70                  75                  80

Gln Thr Gly Arg Ile Gly Asp Gly Lys Ile Phe Val Ser Asn Ile Glu
                85                  90                  95

Glu Ala Ile Arg Ile Arg Thr Gly Glu Ser Gly Leu Asp Ala Ile
            100                 105                 110

(2) INFORMATION FOR SEQ ID NO: 7:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

Met Lys Lys Ile Glu Ala Ile Ile Lys Pro Phe Lys Leu Asp Glu Val
1               5                   10                  15

Lys Glu Ala Leu His Glu Val Gly Ile Lys Gly Ile Thr Val Thr Glu
            20                  25                  30

Ala Lys Gly Phe Gly Arg Gln Lys Gly His Thr Glu Leu Tyr Arg Gly
        35                  40                  45

-continued

```
Ala Glu Tyr Val Val Asp Phe Leu Pro Lys Val Lys Ile Glu Val Val
 50                  55                  60

Met Glu Asp Ser Leu Val Glu Arg Ala Ile Glu Ala Ile Gln Gln Ala
 65                  70                  75                  80

Ala His Thr Gly Arg Ile Gly Asp Gly Lys Ile Phe Val Thr Pro Val
                 85                  90                  95

Glu Glu Val Val Arg Ile Arg Thr Gly Glu Lys Gly Gly Asp Ala Ile
            100                 105                 110
```

(2) INFORMATION FOR SEQ ID NO: 8:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

```
Met Lys Lys Val Glu Ala Ile Ile Lys Pro Phe Lys Leu Asp Glu Val
  1                  5                  10                  15

Lys Glu Ala Leu Gln Glu Ala Gly Ile Gln Gly Leu Ser Val Ile Glu
                 20                  25                  30

Val Lys Gly Phe Gly Arg Gln Lys Gly His Thr Glu Leu Tyr Arg Gly
                 35                  40                  45

Ala Glu Tyr Val Val Asp Phe Leu Pro Lys Val Lys Ile Glu Met Val
 50                  55                  60

Leu Pro Asp Glu Met Val Asp Ile Ala Ile Glu Ala Ile Val Gly Ala
 65                  70                  75                  80

Ala Arg Thr Glu Lys Ile Gly Asp Gly Lys Ile Phe Val Ser Ser Ile
                 85                  90                  95

Glu Gln Ala Ile Arg Ile Arg Thr Gly Glu Thr Gly Glu Asp Ala Val
            100                 105                 110
```

(2) INFORMATION FOR SEQ ID NO: 9:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

```
Met Lys Lys Ile Glu Ala Ile Ile Arg Pro Phe Lys Leu Asp Glu Val
  1                  5                  10                  15

Lys Ile Ala Leu Val Asn Ala Gly Ile Val Gly Met Thr Val Ser Glu
                 20                  25                  30

Val Arg Gly Phe Gly Arg Gln Lys Gly Gln Thr Glu Arg Tyr Arg Gly
                 35                  40                  45

Ser Glu Tyr Thr Val Glu Phe Leu Gln Lys Leu Lys Leu Glu Ile Val
 50                  55                  60

Val Glu Asp Ala Gln Val Asp Thr Val Ile Asp Lys Ile Val Ala Ala
 65                  70                  75                  80

Ala Arg Thr Gly Glu Ile Gly Asp Gly Lys Ile Phe Val Ser Pro Val
                 85                  90                  95

Asp Gln Thr Ile Arg Ile Arg Thr Gly Glu Lys Asn Ala Asp Ala Ile
            100                 105                 110
```

(2) INFORMATION FOR SEQ ID NO: 10:

(i) SEQUENCE CHARACTERISTICS:
        (A) LENGTH: 105 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

Met Lys Met Ile Lys Ala Ile Val Arg Pro Asp Lys Val Asp Asp Ile
 1               5                  10                  15

Val Asp Ser Leu Glu Asn Ala Gly Tyr Pro Ala Phe Thr Lys Ile Asn
            20                  25                  30

Ser Val Gly Arg Gly Lys Gln Gly Gly Leu Lys Val Gly Glu Ile Phe
        35                  40                  45

Tyr Asp Glu Leu Pro Lys Thr Ile Leu Leu Ile Ala Val Asn Asp Asp
50                  55                  60

Glu Val Asp Glu Val Val Gly Leu Ile Lys Ser Ser Ala Ser Thr Gly
65                  70                  75                  80

Asn Phe Gly Asp Gly Lys Ile Phe Ile Gln Pro Ile Thr Glu Ala Tyr
                85                  90                  95

Thr Ile Arg Thr Gly Glu Thr Gly Ile
                100                 105

(2) INFORMATION FOR SEQ ID NO: 11:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:

Met Lys Glu Val Ile Ala Ile Ile Arg Pro Asn Thr Val Ser Lys Thr
 1               5                  10                  15

Val Lys Ala Leu Asp Val Val Gly Phe Pro Ala Val Thr Met Ala Glu
            20                  25                  30

Cys Phe Gly Arg Gly Lys Gln Lys Gly Tyr Glu Glu Gly Glu Lys Glu
        35                  40                  45

Gly Arg Phe Ile Lys Tyr Ile Pro Lys Arg Leu Ile Ser Ile Val Val
50                  55                  60

Asp Asp Ala Asp Val Pro Leu Val Val Gly Ile Ile Ser Lys Val Asn
65                  70                  75                  80

Arg Thr Gly Ser Phe Gly Asp Gly Arg Ile Phe Val Leu Pro Val Glu
                85                  90                  95

Glu Ala Ile Arg Val Arg Thr Gly Glu Thr Gly Glu Ile Ala Ile
                100                 105                 110

(2) INFORMATION FOR SEQ ID NO: 12:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

Phe Ser Ala Asn Leu Pro Glu Ile Val Asp Ile Gln Lys Ile Ile
1               5                   10                  15

(2) INFORMATION FOR SEQ ID NO: 13:

(i) SEQUENCE CHARACTERISTICS:
        (A) LENGTH: 817 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO: 13:

```
CTGAAAGTTG TGTTAAAAAA AAAACTAGAA TCATGGCGGC GTCAATGACG AAACCCATCT      60

CAATAACTTC TCTCGGTTTC TATTCTGATC GAAAGAACAT TGCTTTCTCT GATTGCATTT     120

CGATTTGTTC TGGATTCAGA CATTCCCGAC CATCTTGCCT CGATTTGGTC ACAAAGTCAC     180

CGAGTAATAA CAGTCGTGTT TTACCTGTCG TTAGTGCCCA AATATCTTCT GATTATATTC     240

CAGACTCGAA ATTTTACAAG GTGGAAGCAA TTGTCAGACC ATGGAGAATC CAGCAAGTTT     300

CATCGGCTTT ACTGAAAATC GGGATTCGAG GTGTTACTGT TTCTGATGTG AGAGGGTTTG     360

GTGCACAAGG AGGTTCTACC GAGAGACACG GTGGCTCTGA GTTCTCGGAA GACAAATTTG     420

TTGCTAAAGT TAAGATGGAA ATCGTTGTTA AGAAAGACCA AGTGGAATCT GTAATCAACA     480

CAATAATTGA AGGAGCAAGG ACAGGAGAGA TTGGTGATGG CAAGATTTTT GTTTTGCCTG     540

TGTCAGATGT CATAAGAGTT AGGACAGGTG AGCGTGGGGA GAAAGCAGAG AAGATGACTG     600

GTGATATGCT TTCACCGTCT TAGGAACAAA CAGAGCTCAA GAATGGTTTT TTTTTTTTTC     660

ATTTCGGTCT CTAGATTCTG CGAATAATAA TGAATGGAGT CTGTGTTTGG TTTCATGTTG     720

AATCGATCAA GATGTGTTTT TAACTGTACA TGAATTATGC AGAAACATCT GTCCTGGTTC     780

TCAGACATCG AAACTCTGTT CCTAATAAAA AAAAAAA                             817
```

(2) INFORMATION FOR SEQ ID NO: 14:

(i) SEQUENCE CHARACTERISTICS:
        (A) LENGTH: 897 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO: 14:

```
GCGGTGTCGG CCGCTCTAGA ACTAGTGGAT CCCCCGGGCT GCAGGAATTC GGCACGAGGC      60

TACTGCGAAA CTGGGCTTGC TCACTCCTCT TCATTCTAAT AACATCAAGA AAGAATTCCC     120

TGTTTTTGAT TTCAGTTTGT TTTGTCCAGA GCTTAGACAT TCTCGGTTTT CTCACTTTAA     180

CACCGCGGTC AAGCGCGTAA GATATGCCCC CGTCGTTCCT GTGATTAATG CCCAAAGCTC     240

GCCTGACTAC ATTCCTGATG CTAAATTCTA CAAAGTGGAA GCAATTCTCA GGCCCTGGCG     300

AGTCTCGCAA GTTCCTCGG CTTTGCTAAA AATTGGTATT CGAGGTGTTA CTGTTTCTGA     360

TGTTCGAGGT TTTGGTGCTC AAGGTGGTTC AACTGAGAGG CAGGGCGGCT CAGAATTTTC     420

TGAAGACAAG TTTGTTGCTA AAGTTAAGAT GGAGATCGTG GTTAGCAAAG ACCAGGTTGA     480

GGATGTTATA GAAAAAATCA TTGAGGAGGC AAGAACTGGA GAGATTGGAG ACGGCAAGAT     540

TTTCTTGCTG CCTGTTTCAG ATGTAATAAG AGTCCGCACT GGTGAGCGGG GTGATAAGGC     600
```

```
TGAGAGGATG ACAGGAGGGC GATCTGACAT GAGTACTTCT GCTTGACTGC TGTGACCAGC      660

AATATAGCAT TCAGGACTAA CTGTCCTTTG AGAAAGCCCC GCCCTTATTA GCCATTATCC      720

AGTATAGCTT GATAATTTGA ATTTTTTGTT TTCTTAACTA AAGAAACAAA GATCTTTTCA      780

TTATCCTGTT GATGATAATT GAAAACGGAA GGATCGCGAA TTTGTTCAAG TGCTTGCAAG      840

ATAAATAACA AGAAGAGGAG TAATGTTAAC AAAAAAAAAA AAAAAAAAAA ACTCGAG        897
```

(2) INFORMATION FOR SEQ ID NO: 15:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

```
ATGGCGGCGT CAATGACGAA ACCCATCTCA ATAACTTCTC TCGGTTTCTA TTCTGATCGA       60

AAGAACATTG CTTTCTCTGA TTGCATTTCG ATTTGTTCTG GATTCAGACA TTCCCGACCA      120

TCTTGCCTCG ATTTGGTCAC AAAGTCACCG AGTAATAACA GTCGTGTTTT ACCTGTCGTT      180

AGTGCCCAAA TATCTTCTGA TTATATTCCA GACTCGAAAT TTTACAAGGT GGAAGCAATT      240

GTCAGACCAT GGAGAATCCA GCAAGTTTCA TCGGCTTTAC TGAAAATCGG GATTCGAGGT      300

GTTACTGTTT CTGATGTGAG AGGGTTTGGT GCACAAGGAG GTTCTACCGA GAGACACGGT      360

GGCTCTGAGT TCTCGGAAGA CAAATTTGTT GCTAAAGTTA AGATGGAAAT CGTTGTTAAG      420

AAAGACCAAG TGGAATCTGT AATCAACACA ATAATTGAAG GAGCAAGGAC AGGAGAGATT      480

GGTGATGGCA AGATTTTTGT TTTGCCTGTG TCAGATGTCA TAAGAGTTAG ACAGGTGAG       540

CGTGGGGAGA AAGCAGAGAA GATGACTGGT GATATGCTTT CACCGTCT                  588
```

(2) INFORMATION FOR SEQ ID NO: 16:

(i) SEQUENCE CHARACTERISTICS:
        (A) LENGTH: 594 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

```
CGGCACGAGG CTACTGCGAA ACTGGGCTTG CTCACTCCTC TTCATTCTAA TAACATCAAG       60

AAAGAATTCC CTGTTTTTGA TTTCAGTTTG TTTTGTCCAG AGCTTAGACA TTCTCGGTTT      120

TCTCACTTTA ACACCGCGGT CAAGCGCGTA AGATATGCCC CCGTCGTTCC TGTGATTAAT      180

GCCCAAAGCT CGCCTGACTA CATTCCTGAT GCTAAATTCT ACAAAGTGGA AGCAATTCTC      240

AGGCCCTGGC GAGTCTCGCA AGTTTCCTCG GCTTTGCTAA AAATTGGTAT TCGAGGTGTT      300

ACTGTTTCTG ATGTTCGAGG TTTTGGTGCT CAAGGTGGTT CAACTGAGAG GCAGGGCGGC      360

TCAGAATTTT CTGAAGACAA GTTTGTTGCT AAAGTTAAGA TGGAGATCGT GGTTAGCAAA      420

GACCAGGTTG AGGATGTTAT AGAAAAAATC ATTGAGGAGG CAAGAACTGG AGAGATTGGA      480

GACGGCAAGA TTTTCTTGCT GCCTGTTTCA GATGTAATAA GAGTCCGCAC TGGTGAGCGG      540

GGTGATAAGG CTGAGAGGAT GACAGGAGGG CGATCTGACA TGAGTACTTC TGCT            594
```

(2) INFORMATION FOR SEQ ID NO: 17:
    (i) SEQUENCE CHARACTERISTICS:
        (A) LENGTH: 20 base pairs
        (B) TYPE: nucleic acid
        (C) STRANDEDNESS: single -continued (D) TOPOLOGY: linear (ii) MOLECULE TYPE: Other (xi) SEQUENCE DESCRIPTION: SEQ ID NO: 17:

GCAAGATGGT CGGGAATGTC                                                    20

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 18:

CGACAGGTAA AACACGACTG                                                    20

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 19:

GGTCTGACAA TTGCTTCCAC                                                    20

(2) INFORMATION FOR SEQ ID NO: 20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 20:

GAAACCAAAC ACAGACTCC                                                     19

(2) INFORMATION FOR SEQ ID NO: 21:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 21:

CCGAGTAATA ACAGTCGTC                                                     19

PLANT NITROGEN REGULATORY P-PII POLYPEPTIDES

This is a continuation of application Ser. No. 08/899,330, filed Jul. 23, 1997 now U.S. Pat. No. 6,177,275.

This invention was made with U.S. government support under National Institute of Health grant number GM32877 and Department of Energy grant number DE-FG02-94ER20133 and National Science Foundation grant No. DIR-8908095. The U.S. government has certain rights in the invention.

1. INTRODUCTION

The present invention generally relates to a plant nitrogen regulatory PII gene (hereinafter P-PII gene), a gene involved in regulating plant nitrogen metabolism. The invention provides P-PII nucleotide sequences, expression constructs comprising said nucleotide sequences, and host cells and plants having said constructs and, optionally expressing the P-PII gene from said constructs. The invention also provides substantially pure P-PII proteins.

The P-PII nucleotide sequences and constructs of the invention may be used to engineer organisms to overexpress wild-type or mutant P-PII regulatory protein. Engineered plants that overexpress or underexpress P-PII regulatory protein may have increased nitrogen assimilation capacity. Engineered organisms may be used to produce P-PII proteins which, in turn, can be used for a variety of purposes including in vitro screening of herbicides. P-PII nucleotide sequences have additional uses as probes for isolating additional genomic clones having the promoters of P-PII gene. P-PII promoters are light- and/or sucrose-inducible and may be advantageously used in genetic engineering of plants.

2. BACKGROUND OF THE INVENTION

Plants can assimilate soil ammonia or nitrate reduced to ammonia into organic form in leaves or roots. Ammonia assimilation into glutamine and glutamate occurs primarily in leaf chloroplasts or in root plastids by the combined action of chloroplast glutamine synthetase (GS2; GLN2 gene) and glutamate synthase (GOGAT) (Miflin, B. J. & Lea, P. J., 1977, Ann. Rev. Plant Physiol. 28:299–329). As the assimilation of inorganic nitrogen into organic form requires carbon skeletons, reducing equivalents, and ATP, light serves to coordinate nitrogen assimilation with photosynthesis. Genes involved in plant nitrogen assimilation are induced directly by light (via phytochrome), as well as indirectly by metabolic changes in photosynthate. For example, it has been shown that sucrose supplementation to plant growth media can at least partially induce the expression of mRNA for GLN2 or nitrate reductase (NR) in the absence of light (Cheng et al., 1992, Proc. Natl. Acad. Sci. USA. 89:1861–1864; Faure et al., 1994, Plant J. 5:481–491). Conversely, sucrose can repress the expression of asparagine synthetase (ASN1) (Lam et al., 1994, Plant Physiol. 106:1347–1357). More recently, it has been shown that the effects of sucrose on gene expression can be reversed by the addition of an organic nitrogen source both for nitrate reductase (NR) (Vincentz et al., 1993, Plant J. 3:315–324) and for ASN1 (Lam et al., 1994, Plant Physiol. 106:1347–1357). These findings indicate that plants are able to sense levels of carbon and organic nitrogen, and in turn modulate the expression of genes involved in nitrogen assimilation.

Bacteria can also assimilate ammonia into glutamate or glutamine. Plants' ability to sense changes in the levels of carbon and nitrogen metabolites is reminiscent of a nitrogen regulatory system (Ntr) in bacteria in which a protein called PII, encoded by the glnB gene, can regulate the assimilation of nitrogen into glutamine via glutamine synthetase (GS; glnA) in response to changes in the ratio of organic nitrogen to carbon metabolites (Magasanik, B., 1994, J. Cell. Biochem. 51:34–40).

In response to changes in the metabolic status (i.e., ratio of glutamine to α-ketoglutarate [gln/α-KG]), the PII protein of bacteria interacts with a set of partners to regulate the glnA gene at the transcriptional level, and to regulate GS enzyme activity at the post-translational level (Magasanik, B., 1994, J. Cell. Biochem. 51:34–40). Changes in the gln/α-KG ratio affect the activity of the PII protein via a post-translational modification (uridylylation) at Tyr51 (Magasanik, B., 1988, TIBS 13:475–479). In response to low gln/α-KG, the PII protein is uridylylated by uridylyltransferase (UTase) (id.). The PII-UMP thus formed then interacts with an adenylyltransferase (ATase) to deadenylylate the GS-AMP enzyme and thereby activate the GS enzyme (Magasanik, B., 1994, J. Cell. Biochem. 51:34–40). A high gln/α-KG ratio causes the deuridylylation of PII-UMP. This unmodified form of PII interacts with ATase to stimulate the adenylylation and inactivation of the GS enzyme. The ability of ATase to attach or remove AMP from the GS enzyme is dependent on the interaction of ATase with PII or PII-UMP, respectively (Foor et al., 1975, Proc. Natl. Acad. Sci. USA 72:4844–4848). Thus, the nitrogen-regulatory protein PII, is a signal transducer whose post-translational modification indirectly regulates GS enzyme activity post-translationally. In addition to its ability to regulate the GS holoenzyme activity, PII can also interact with a two-component system (NRII/NRI, or NtrB/NtrC) to regulate the transcription of the glnA gene encoding GS (Magasanik, B., 1994, J. Cell. Biochem. 51:34–40). Under low gln/α-KG levels, NRII-kinase phosphorylates NRI which then interacts with the $\sigma^{54}$ to activate glnA gene expression (Ninfa, A. J. and Magasanik, B., 1986, Proc. Natl. Acad. Sci. USA 83:5909–5913). When the gln/α-KG ratio is high, the interaction of PII with NRII stimulates the NRII-phosphatase activity to dephosphorylate NRI-phosphate, and turn off the inducible promoter of glnA transcription (Ninfa, A. J. and Magasanik, B., 1986, Proc. Natl. Acad. Sci. USA 83:5909–5913). Thus, the nitrogen-regulatory protein PII works in concert with other proteins, including UTase, ATase, NRII, and NRI, to regulate glutamine synthetase enzyme activity or glnA transcription in response to the ratio of organic nitrogen to carbon metabolites (Magasanik, B., 1994 J. Cell. Biochem. 51:34–40).

To date, PII homologues have been identified in a diverse set of bacteria including enteric bacteria (Magasanik, B., 1994, J. Cell. Biochem. 51:34–40), cyanobacteria (Tsinoremas et al., 1991, Proc. Natl. Acad. Sci. USA 88:4565–4569), *Bacillus* (Wray et al., 1994, J. Bacteriol. 176:108–114), and in archaebacteria (Souillard, N. and Sibold, L., 1989, Mol. Microbiol. 3:541–551).

3. SUMMARY OF THE INVENTION

The present invention relates to a plant nitrogen regulatory P-PII gene involved in regulating nitrogen assimilation in plants. The invention provides P-PII coding nucleotide sequences, expression constructs comprising P-PII coding sequences, and host organisms, including plants, containing said expression constructs. The invention also provide P-PII proteins.

The invention is based on the surprising discovery that plants have a structural homolog, P-PII, to the bacterial PII protein. This is the first time a PII-like gene has been identified in an eukaryote. The regulation of P-II mRNA levels by light and by metabolites, such as sucrose, parallels those of nitrogen assimilatory genes such as chloroplastic GS2 (GLN2). See Faure et al., 1994, *Plant J.* 5:481–491; Edwards, J. W. and Coruzzi, G. M., 1989, Plant Cell 1:241–248; Lam et al., 1994, Plant Physiol. 106:1347–1357; Vincentz et al., 1993, Plant J. 3:315–324. These findings indicates that like bacterial PII, P-PII protein is a plant nitrogen regulatory protein that controls the expression of nitrogen assimilation functions.

The P-PII nucleotide sequences and constructs of the invention may be advantageously used to engineer plants to overexpress P-PII regulatory protein. P-PII overexpression or underexpression should enhance the levels of certain nitrogen assimilation functions and thereby increase nitrogen utilization efficiencies of engineered plants.

P-PII nucleotide sequences and constructs of the invention also may be used to engineer organisms to overexpress wild-type or mutant P-PII regulatory protein. Full length cDNAs for P-PII can be used in a "reverse biochemical" approach to synthesize and characterize the encoded P-PII proteins. The ability to use the cloned P-PII to synthesize the purified P-PII proteins will allow a characterization of P-PII protein in terms of physical properties (i.e., inducer or activator preference) and subcellular localization (i.e., plastid vs. cytosol).

Full length P-PII cDNA clones may also be used to synthesize highly purified preparations of the wild-type or altered P-PII in vitro or in vivo (e.g., bacteria, algae, neurospora, yeast, plant, or animal cells). In vitro or in vivo synthesized P-PII protein can be used as a substrate in a screen to identify novel herbicidal compounds, which selectively inhibit this nitrogen regulatory protein. The isolated cDNAs encoding P-PII may also be used to create plants resistant to such herbicides.

Nucleic acids, DNA or RNA, encoding P-PII have additional uses as probes for isolating additional genomic clones having the promoters of P-PII genes. P-PII promoters are light- /or sucrose-inducible and may be advantageously used in genetic engineering of plants. For example, P-PII promoters may be used to directly express genes encoding functions that P-PII proteins directly or indirectly activate or induce. P-PII promoter sequences also may be used to construct chimeric promoters.

3.1. ABBREVIATIONS AND DEFINITIONS

The following terms as used herein, whether in the singular or plural, shall have the meanings indicated.

| | |
|---|---|
| Asn = | asparagine |
| AS = | asparagine synthetase |
| bp = | basepair |
| chimeric gene = | A chimeric gene comprises a coding sequence linked to a promoter that said coding sequence is not naturally linked to. The coding sequence may encode messenger RNA (mRNA), antisense RNA or ribozymes. As used herein the term is meant to encompass only artificially produced genes using genetic selection or recombinant DNA methodologies and not any genes found in wild-type organisms or cells not subjected to experimentation |
| EDTA = | disodium ethylene diamine tetracetate |
| GLB1 = | the gene encoding P-PII protein |
| GS = | glutamine synthetase |

3.1. ABBREVIATIONS AND DEFINITIONS

The following terms as used herein, whether in the singular or plural, shall have the meanings indicated.

| | |
|---|---|
| GUS = | 1,3-β-Glucuronidase |
| heterologous = | unrelated, e.g., not of the same gene or organism |
| kb = | kilobase |
| operably linked = | The linkage between a promoter and a coding sequence such that the promoter controls the transcription of the coding sequence |
| PCR = | polymerase chain reaction |
| P-PII = | plant PII |
| poly (A) = | polyadenylate |
| recombinant = | resulting from artificial, genetic-engineering efforts and not natural mutational events |
| SDS = | sodium dodecyl sulfate |
| 20 × SSC = | 175.3 g NaCl and 88.2 g sodium citrate in 800 ml $H_2O$, pH 7.0 (adjusted with 10 N NaOH), adjusted to 1 liter. |

Peptide and polypeptide sequences defined herein are represented by one-letter symbols for amino acid residues as follows:

A (alanine)
R (arginine)
N (asparagine)
D (aspartic acid)
C (cysteine)
Q (glutamine)
E (glutamic acid)
G (glycine)
H (histidine)
I (isoleucine)
L (leucine)
K (lysine)
M (methionine)
F (phenylalanine)
P (proline)
S (serine)
T (threonine)
W (tryptophan)
Y (tyrosine)
V (valine)

4. BRIEF DESCRIPTION OF THE FIGURES

FIG. 1. Comparison of the deduced amino acid sequences of plant PII and microbial PII pcdypeptides. FIG. 1A. The amino acid residues conserved between all microbial PIIs and plant PII are shaded. The asterisks (*) indicate residues conserved between plant and any bacterial PII. Boxed areas labeled I and II include residues of two PII signature domains conserved between all PIIs. The position of the tytosine residue (Tyr 51) which is uridylylated in *E. ccli* is indicated by an arrow. The PII sequences shown in this figure are: At, *Arabidopsis thaliana* (SEQ ID NO:1); Ric, *Ricinus communis* (SEQ ID NO:2); Kp, *Klebsiella pneumoniae* (SEQ ID NO:3); Ec, *Escherichia coli* (SEQ ID NO:4); R1, *Rhizobium leguminosarum* (SEQ ID NO:5); Bj, *Bradyrhizobium japonicum* (SEQ ID NO:6); Az, *Azospirillum brasilense* (SEQ ID NO:7); Rc, *Rhodobacter capsulatus* (SEQ ID NO:8); Sy, *Synechococcus* (SEQ ID NO:9) strain PCC 7942; Mtl, *Methanococcus thermolithotrophicus* glnB-like protein 1 (SEQ ID NO:10) Mt2, *Methanococcus thermolithotrophicus* glnB-like protein 2 (SEQ ID NO:11). For best alignment of Mt2 with glnB, the last two residues, BN, and the peptide sequence FSANLPEIVDIQKII (SEQ ID NO:12) are deleted. This deletion is indicated by "^" in the Mt2 sequence. The numbers 1, 51, and 112 indicate the residue positions of the *E. coli* PII protein. FIG. 1B. The relationship between plant PII and microbial PIIs is shown by a phylogenetic analysis using parsimony. Bacillus PII-like protein is an anomoly which does not cluster with bacterial taxa. F, phenylanaline; Y, tyrosine.

Figure 2:
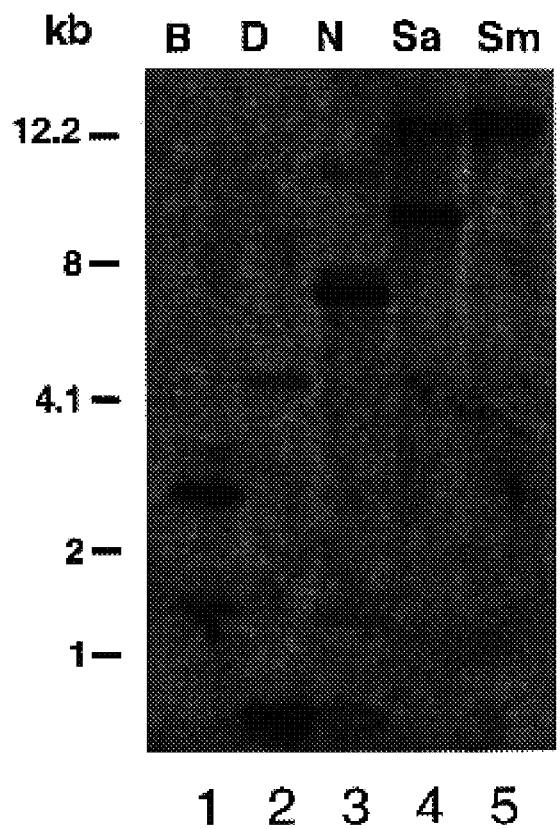

FIG. 2. Southern blot analysis of GLB1 gene in *Arbidopsis* genomic DNA. *Arabidopsis thaliana* (Columbia ecotype) genomic DNA was digested with the following restriction enzymes; B. BglII (lane 1); D, DraI (lane 2); N, NdeI (lane 3); Sa, 5SacI (lane 4); Sm, SmaI (lane 5), resolved by gel electrophoresis, transferred to Hybond-N membrane and probed with DIG-labeled single-stranded probe derived from the *Arabidopsis* GLB1 cDNA.

Figure 3:
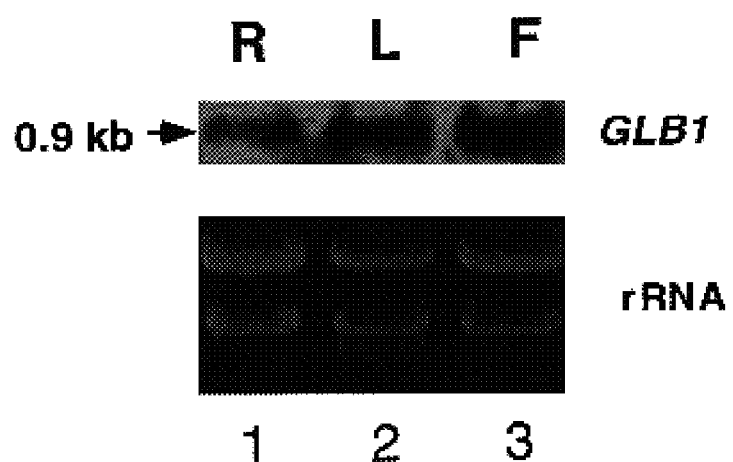

FIG. 3. Northern blot analysis of *Arabidopsis* GLB1 mRNA levels in different organs. Total RNA (20 µg) from roots (lane 1), leaves (lane 2) and flowers (lane 3) was detected with DIG-labeled single-stranded DNA probe derived from Arabidopsis GlB1 cDNA. Roots and leaves were from 6-week-old mature plants. Flowers were buds or developing flowers.

Figure 4A:
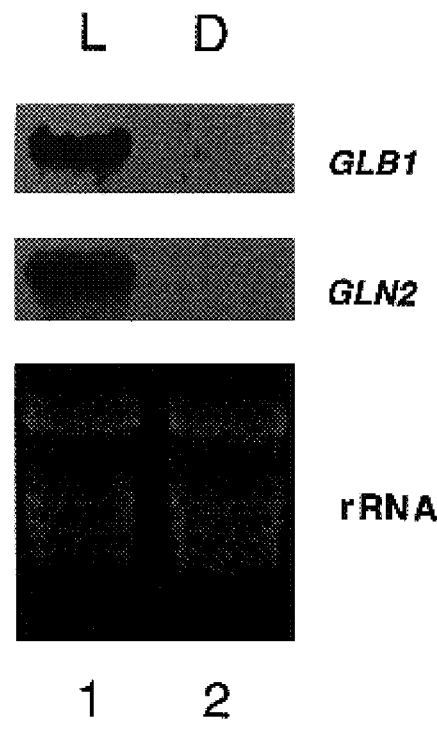
Figure 4B:
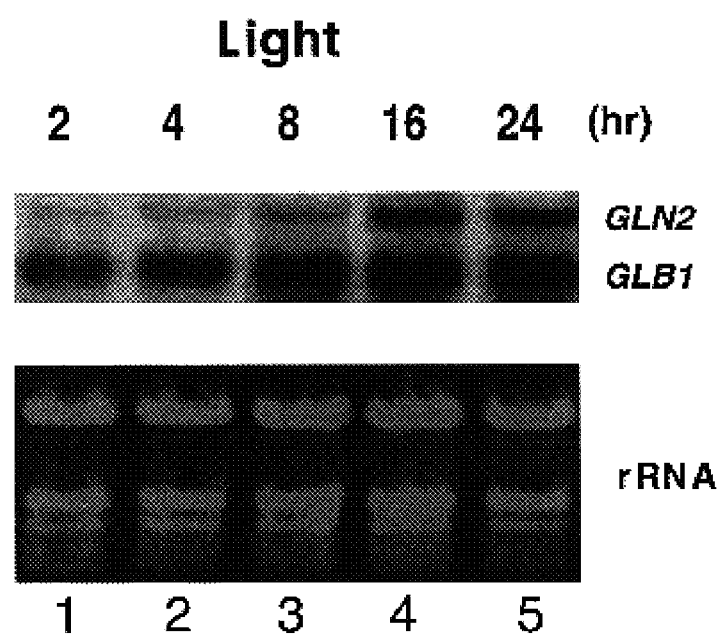

FIG. 4. Light-induced expression of *Arabidopsis* GLB1 gene. FIG. 4A. Total RNA (20 µg) from leaves of light-grown (L; lane 1) or dark-adapted (D; lane 2) mature *Arabidopsis* plants. GLN2 and ASN1 mRNAs were also detected on duplicate Northern blots as controls for RNA preparation. FIG. 4B. Time-course of light-induction of GLB1 mRNA in *Arabidopsis*. Total RNA (10µ) from two-week-old *Arabidopsis* plants grown in semi-hydroponics which were dark-adapted for two days and then exposed to light for 2 hr (lane 1), 4 hr (lane 2), 8 hr (lane 3), 16 hr (lane 4), and 24 hr (lane 5). *Arabidopsis* DNA probes for GLB1 and GLN2 cDNAs were used to detect mRNAs on the identical Northern blot simultaneously.

Figure 5:
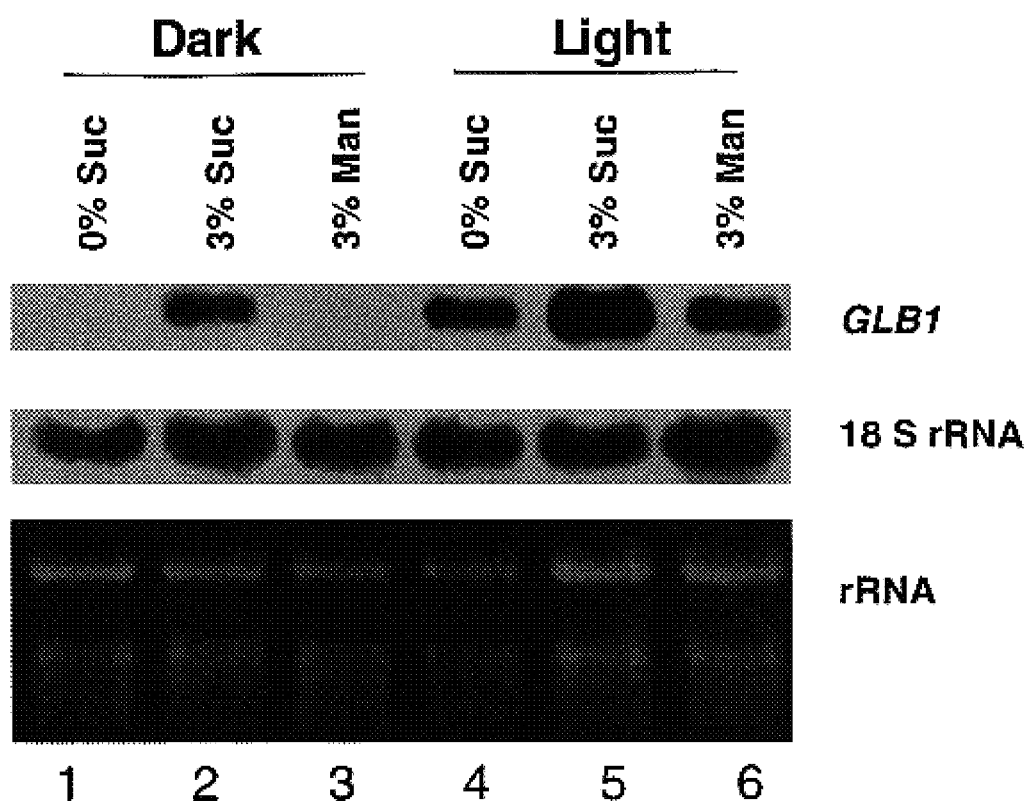

FIG. 5. Sucrose-induced expression of *Arabidopsis* GLB1 gene. Total RNA (10 µg) from two-week-old Arabidopsis plants dark-spotted (lanes 1–3) or light-grown (lanes 4–6) for two days was used for Northern blot analysis. During the dark- or light-treatments, plants were grown in media containing 0% sucrose (lanes 1 and 4), 3% sucrose (lanes 2 and 5) or 3% mannitol (lanes 3 and 6. As a control, 18 S ribosomal RNA was detected on a replicate blot. The ethidium bromide staining of the RNA in the agarose gel before transfer is also shown.

Figure 6:
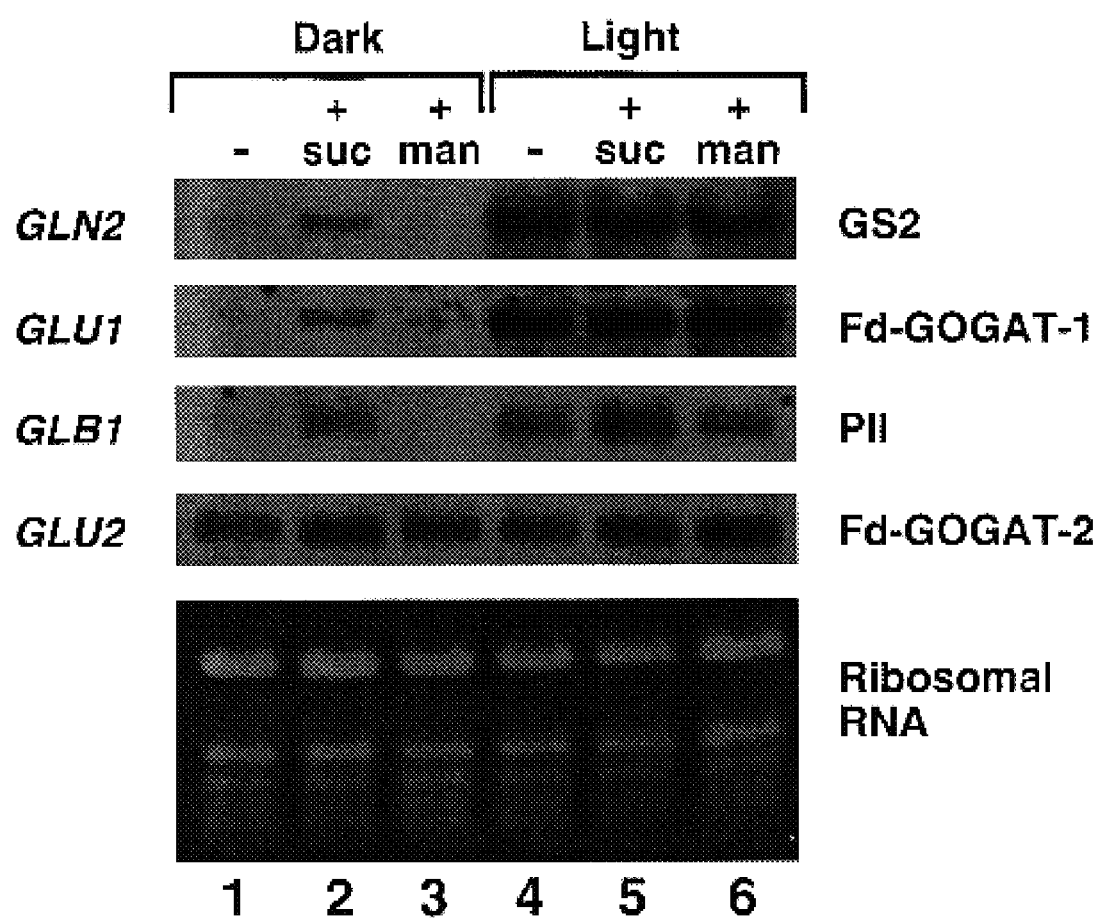

FIG. 6. PII (GLB1) mRNA is induced by light and/or high sucrose. Induction of PII (GLB1) mRNA by light/sucrose mirrors that of the putative downstream target nitrogen assimilatory genes GS2 (GLN2) and Fd-GOGAT (GLU1). PII mRNA is low in dark-adapted plants (lane 1) and is induced by sucrose in the absence of light (lane 2), but not by mannitol, a non-metabolizable sugar (lane 3). Light induces PII mRNA (lane 4). Light plus sucrose super-induces PII mRNA (lane 5). Mannitol cannot superinduce PII mRNA above light levels (lane 6). Nitrogen assimilatory genes GS2 and Fd-GOGAT GLU1, also show induction by sucrose (lane 2) or light (lane 3), but are not super-induced by light and sucrose (lane 5).

Figure 7:
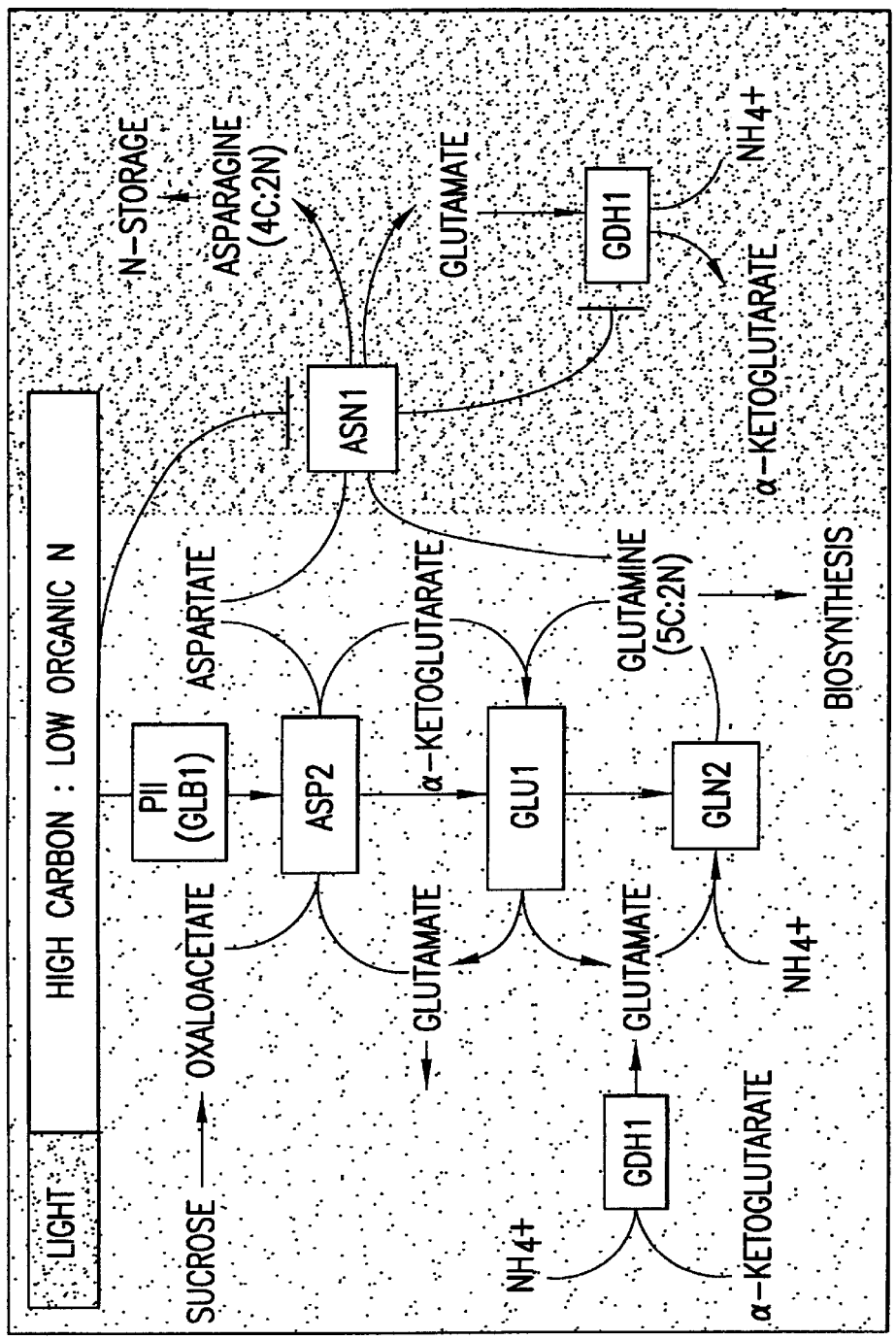

FIG. 7. Metabolic control model whereby light or high sucrose induces PII (GLB1) and putative downstream nitrogen assimilatory genes. PII induction by light and/or high sucrose, mirrors the induction of downstream nitrogen assimilatory genes for glutamine synthetase (GLN2), Fd-dependent glutamate synthase (Fd-GOGAT, GLU2), and aspartate aminotransferase (ASP2). By contrast, genes for asparagine synthetase (ASN1) and glutamate dehydrogenase are repressed by high sucrose (Lam et al, 1994 plant physiol. 106: 1347–1357).

Figure 8:
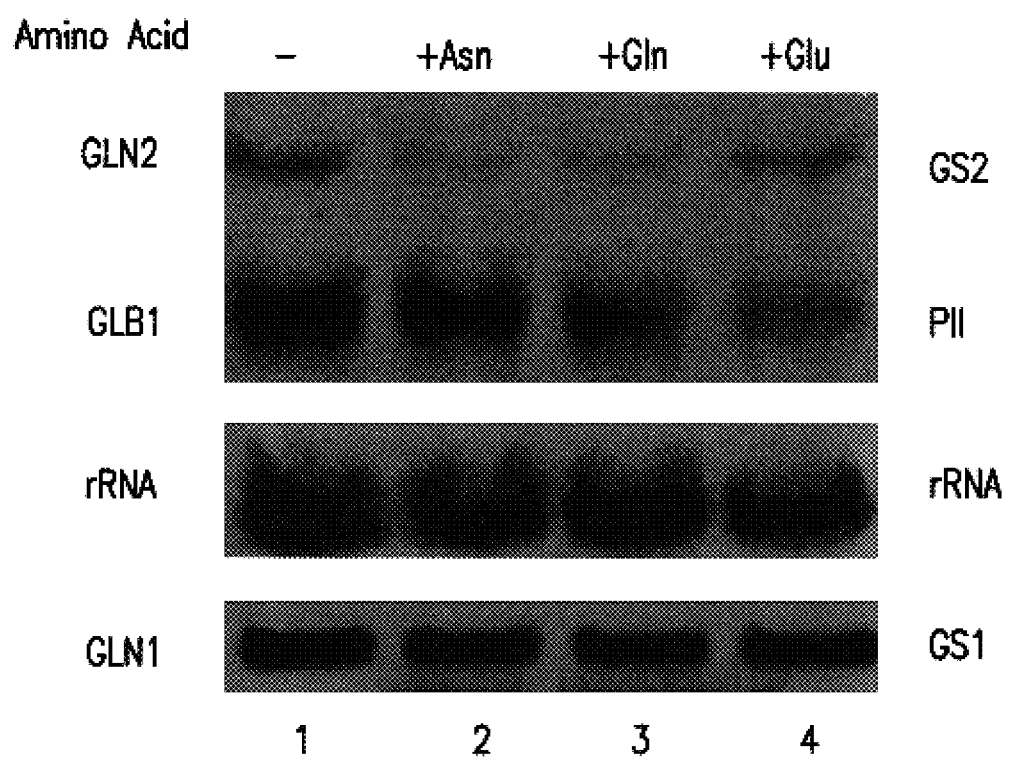

FIG. 8. PII (GLB1) expression is repressed by high organic nitrogen, relative to carbon. Sucrose induction of PII (GLB1) mRNA (lane 1) is repressed by addition of organic nitrogen (lanes 2–4). This regulation of PII mirrors the regulation of the putative downstream nitrogen assimilatory gene for glutamine synthetase (GLN2).

Figure 9:
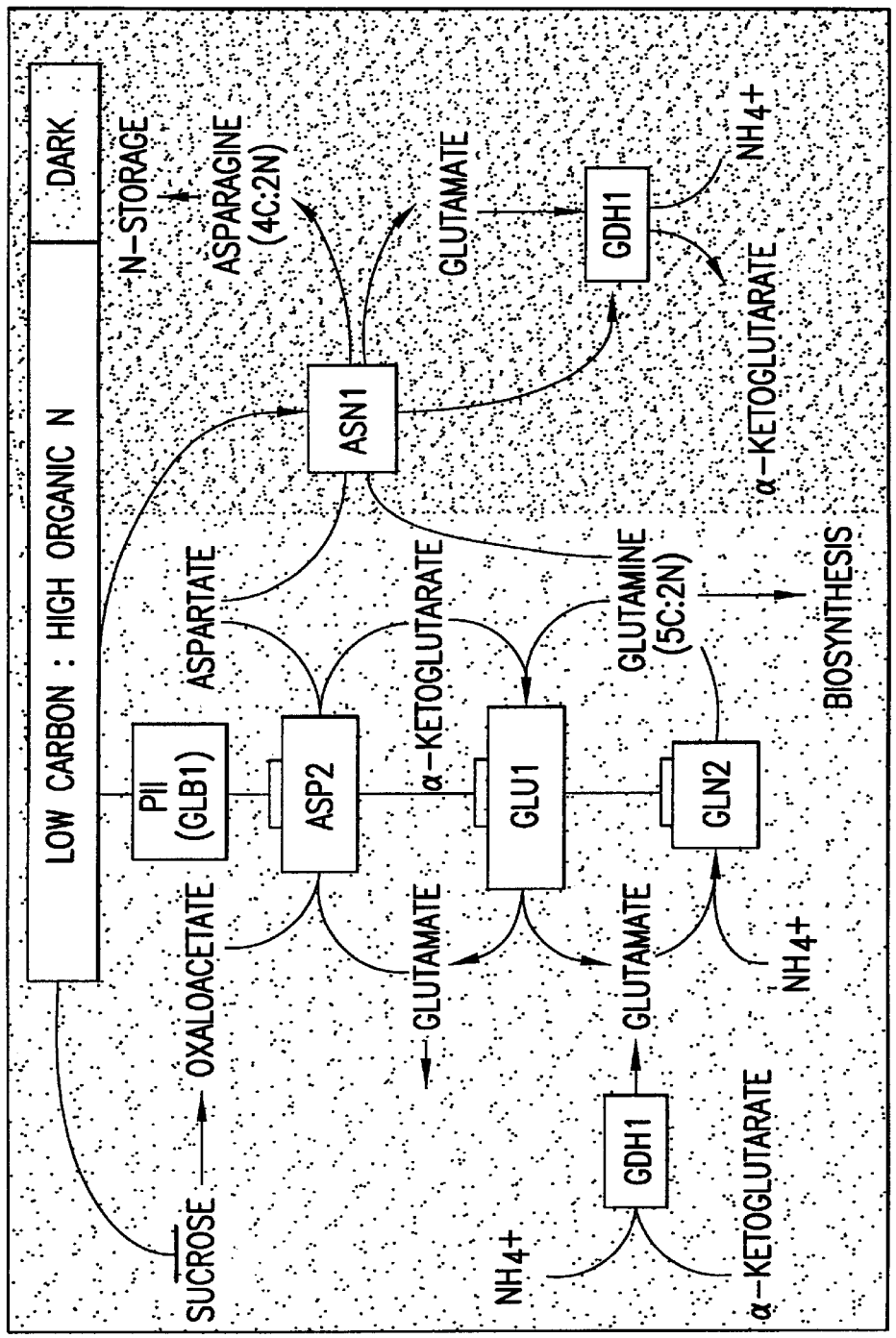

FIG. 9. Metabolic control model whereby dark or high organic nitrogen/low carbon represses PII (GLB1). PII and its putative downstream nitrogen assimilatory genes (GLN2, GLU1 and ASP2) are induced by sucrose (lane 1). Sucrose induction is repressed by addition of organic nitrogen as asparagine (lane 2), glutamine (lane 3) and glutamate (lane 4). By contrast, ASN1 (Lam et al, 1994 plant physiol. 106: 1347–1357). and GDH1 are induced by these conditions.

Figure 10:
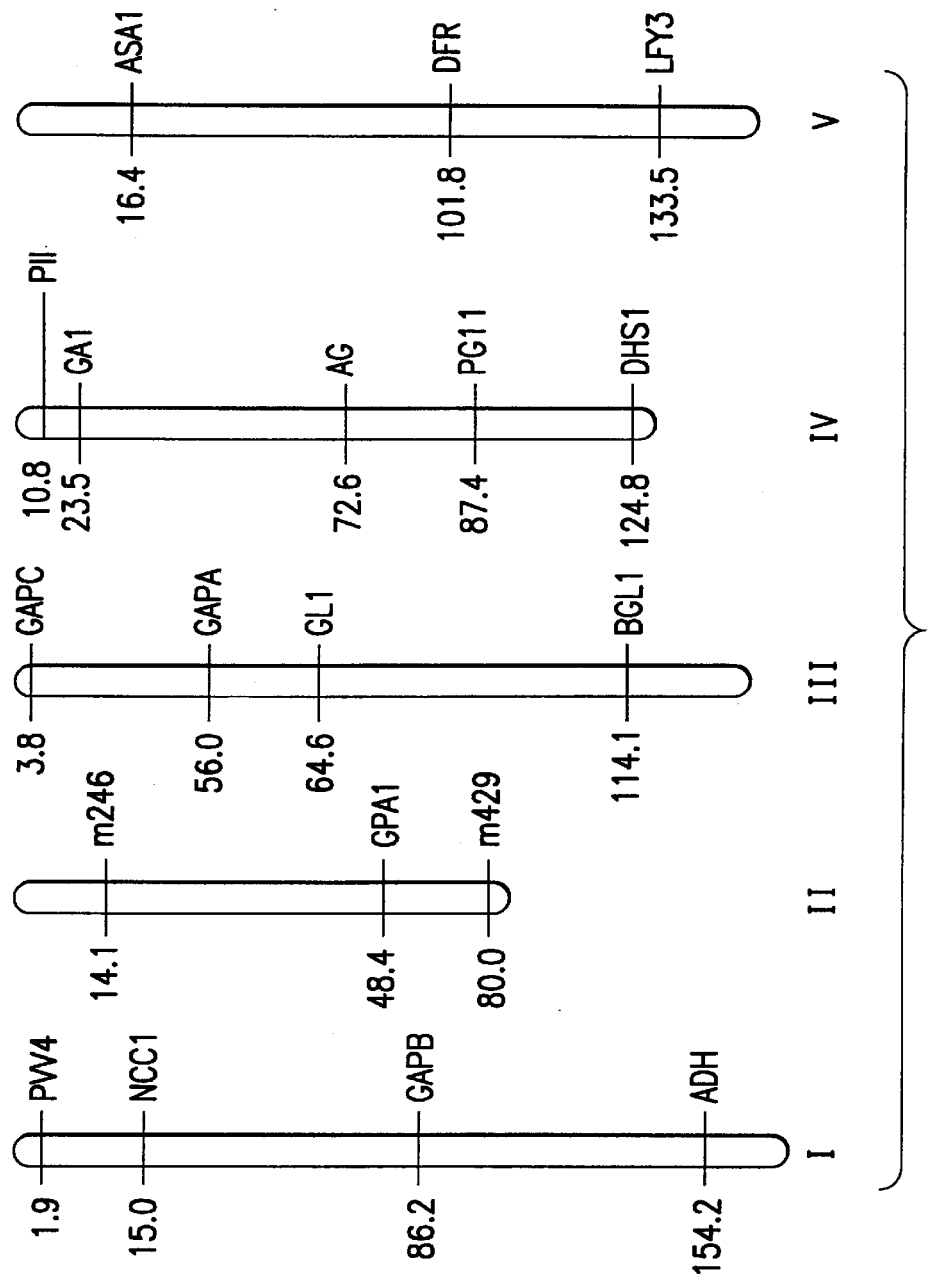

FIG. 10. Arabidopsis PII (GLB1) gene maps to the top arm of chromosome 4. RFLP and recombinant inbred lines of Arabidopsis to map the PII (GLB1) gene to the top arm of chromosome 4 at position 10.8.

Figure 11:
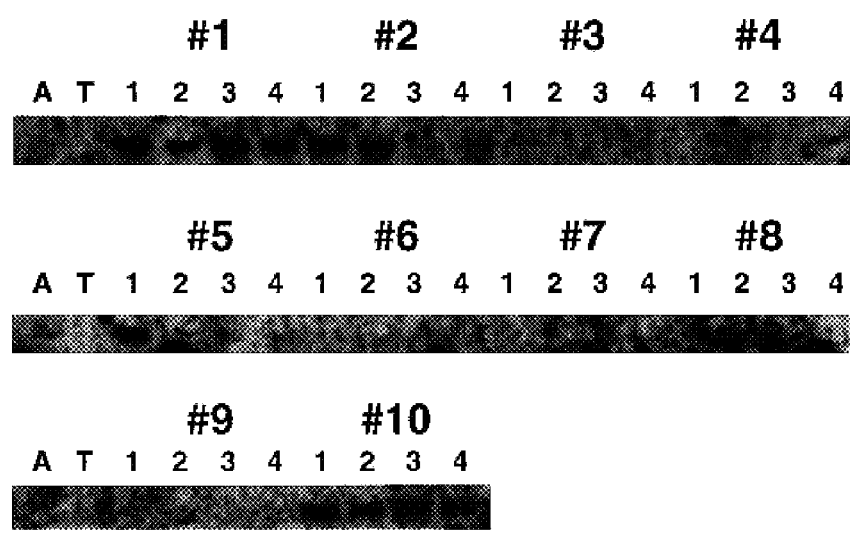

FIG. 11. Transgenic tobacco plants expressing antisense PII mRNA. Antisense *Arabidopsis* PII was introduced into tobacco by Agrobacterium-mediated DNA transfer. Shown are four independent transgenic tobacco lines which express high levels of PII antisense RNA (lines 1, 2, 5 and 10).

FIG. 12. Nucleotide sequence of *Arabidopsis* P-PII cDNA clone (SEQ ID NO:13).

FIG. 13. Nucleotide sequence of *Ricinus* Castor Bean P-PII cDNA clone (SEQ ID NO:14).

5 DETAILED DESCRIPTION OF THE INVENTION

The present invention relates to the plant PII (P-P-II; GLB1) gene. The invention provides nucleotide sequence encoding P-PII protein, expression constructs that can be used to express or overexpress P-PII, and organisms engineered with P-PII expression constructs. The invention also provides P-PII proteins.

In accordance with one aspect of the invention, biologically active P-PII may be produced by the cloning and expression of the nucleotide coding sequence for P-PII or its functional equivalent in appropriate host cells. Successful expression and production of purified P-PII using the full length cDNA clones described and exemplified herein is significant since this regulatory protein has yet to be isolated or purified from plants.

The synthesis of purified P-PII protein via genetic engineering techniques which provide for the expression of full length cDNAs may be utilized to obtain antibodies specific for P-PII which will enable the characterization of related proteins and subcellular localizations of P-PII in plant cells. The recombinantly produced P-PII protein can be advantageously used to screen in vitro for compounds that activates or inhibits the protein's activity. Due to P-PII's role in regulating a critical metabolic process, such activators and inhibitors are candidate positive or negative plant growth regulatory compounds, (negative plant growth regulators include herbicides).

The cloned P-PII cDNAs expressed by microorganisms can be used to screen and identify new plant growth regulatory compounds and to screen and/or select P-PII variants. For example, P-PII cDNAs genetically altered and expressed in microorganism can be used to screen and/or select altered P-PII proteins which are more sensitive to inducers or constitutively active (i.e., active without the need for light- or sucrose induction). Gene constructs encoding such altered P-PII may be used in genetic-engineering to enhance the nitrogen assimilation capabilities of plants.

The invention may be divided into the following stages solely for the purpose of description and illustration: (A) isolation or generation of the coding sequence for P-PII gene(s); (b) construction of an expression vector which will direct the expression of the P-PII coding sequences; (c) transfection of appropriate hosts which are capable of replicating and expressing the P-PII coding sequences to produce biologically active gene products; and (d) identification and/or purification of the P-PII so produced. Once a transformant or transfectant is identified that expresses high levels of biologically active P-PII, the practice of the invention involves the expansion of that clone and the use of that clone in the production of P-PII, the selection of novel plant growth regulators that effect their action through P-PII, and/or the engineering of transgenic plants.

Another aspect of the invention involves the use of the P-PII promoter to direct the expression of heterologous coding sequences. Light or sucrose activates the P-PII promoter in various organs, including shoots, roots and flower. Thus, this promoter can be used to direct the regulated expression of heterologous gene sequences in appropriate hosts.

The invention is demonstrated herein, by way of examples in which cDNAs of P-PII were prepared, cloned and characterized. P-PII cDNA and genomic clones may be isolated using homologous P-PII sequences obtained from related plants. Various aspects of the invention are described in more detail in the subsections below and in the examples that follow.

5.1. P-PII Coding Sequences

The nucleotide coding sequences for *Arabidopsis* and castor bean P-PII are depicted in FIGS. 12 and 13, respectively. These nucleotide sequences, or fragments or functional equivalents thereof, may be used to generate recombinant DNA molecules that direct the expression of the P-PII gene product, or functionally active peptides or functional equivalents thereof, in appropriate host cells.

The nucleotide sequences encoding the castor bean P-PII gene and the *arabidopsis* P-PII gene can be used to screen cDNA libraries obtained from other plant species to identify further plant P-PII genes. A plant cDNA library may be screened under conditions of reduced stringency, using a radioactively or nonradioactively labeled fragment of the castor bean or the *Arabidopsis* P-PII clone. Alternatively, the *Arabidopsis* P-PII or the castor bean P-PII sequences can be used to design degenerate or fully degenerate oligonucleotide probes which can be used as PCR probes or to screen plant cDNA libraries. Alternatively, the probes may be used to screen genomic libraries.

The P-PII nucleotide sequences of the invention include (a) the DNA sequence in FIG. 12 (SEQ ID NO:13); (b) the DNA sequence spanning from nucleotide 33 to 620 as shown in FIG. 12 (SEQ ID NO:15); (c) the DNA sequence in FIG. 13 (SEQ ID NO:14), (d) the DNA sequence spanning from nucleotide 50 to 643 as shown in FIG. 13 (SEQ ID NO:16); (e) any nucleotide sequence that hybridizes to the complement of the DNA sequence shown in FIG. 12 and encodes a functionally equivalent product; and (f) any nucleotide sequence that hybridizes to the complement of the DNA sequence shown in FIG. 13 and encodes a functionally equivalent product. Functional equivalents of the P-PII include naturally occurring P-PII in other plant species, the mutant P-PII whether naturally occurring or engineered. The invention also includes degenerate variants of sequences (a) through (f).

The invention also includes nucleic acid molecules, preferably DNA molecules, that hybridize to, and are therefore complements of, the nucleotide sequences (a) through (f), in the preceding paragraph. Such hybridization conditions may be highly stringent or less highly stringent. In instances wherein the nucleic acid molecules are deoxyoligonucleotides ("oligos"), highly stringent conditions may refer, e.g., to washing in 6×SSC/0.5% sodium pyrophosphate at 37° C. (for 17-base oligos), 55° C. (for 20-base oligos), and 60° C. (for 23-base oligos). These nucleic acid molecules may encode or act as P-PII antisense, ribozyme and/or triple helix sequences, useful, for example, in P-PII gene regulation.

The P-PII nucleotide sequences of the present invention also include any nucleotide sequence encoding a plant protein containing the amino acid sequences designated At or RIG in FIG. 1A; and (b) any nucleotide sequence that hybridizes to the complement of the DNA sequences that encode the amino acid sequence designated At or RIC in FIG. 1. The invention also includes nucleic acid molecules, preferably DNA molecules, that hybridize to, and are therefore complements of the nucleotide sequences (a) and (b). Such hybridization conditions may be highly stringent or less highly stringent. In addition to the P-PII nucleotide sequences described above, full length P-PII cDNA or gene sequences present in the same species and/or homologs of the P-PII gene present in other plant species can be identified and readily isolated, without undue experimentation, by molecular biological techniques well known in the art. The identification of homologs of P-PII in related species can be useful for developing plant model systems for purposes of discovering activators or inhibitors of P-PII to modify P-PII in plants to alter plant nitrogen metabolism. Alternatively, such cDNA libraries, or genomic DNA libraries derived from the organism of interest can be screened by hybridization using nucleotides described herein as hybridization or amplification probes.

Screening can be by filter hybridization, using duplicate filters. The labeled probe can contain at least 15–30 base pairs of the P-PII nucleotide sequence as shown in FIGS. 12 and 13. The hybridization washing conditions used should be of a lower stringency when the cDNA library is derived from an organism different from the type of organism from which the labeled sequence was derived.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Alternatively, the labeled P-PII nucleotide probe may be used to screen a genomic library derived from the organism of interest, again, using appropriately stringent conditions. The identification and characterization of plant genomic clones is helpful for designing diagnostic tests and clinical protocols for regulating plant growth rate and nitrogen metabolism. For example, sequences derived from regions adjacent to the intron/exon boundaries of the plant gene can be used to design primers for use in amplification assays to detect mutations within the exons, introns, splice sites (e.g. splice acceptor and/or donor sites), etc., that can be used in diagnostics.

Further, a P-PII gene homolog may be isolated from nucleic acid of the organism of interest by performing PCR using two degeneration oligonucleotide primer pools designed on the basis of amino acid sequences within the P-PII gene product disclosed herein. The template for the reaction may be cDNA obtained by reverse transcription of mRNA prepared from, for example, plant cell lines or tissue, known or suspected to express P-PII gene allele.

The PCR product may be subcloned and sequenced to ensure that the amplified sequences represent the sequences of a P-PII gene. The PCR fragment may then be used to isolate a full length cDNA clone by a variety of methods. For example, the amplified fragment may be labeled and used to screen a cDNA library, such as a plant cDNA library. Alternatively, the labeled fragment may be used to isolate genomic clones via the screening of a genomic library.

PCR technology may also be utilized to isolate full length cDNa sequences. For example, RNA may be isolated, following standard procedures, from an appropriate cellular or tissue source (i.e., one known, or suspected, to express the P-PII gene. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

The P-PII gene sequences may additionally be used to isolate mutant P-PII gene alleles. Such mutant alleles may be isolated from plant species either known or proposed to have a genotype which contributes to the plant growth rate or nitrogen metabolism. Mutant alleles and mutant allele products may then be utilized in the therapeutic and diagnostic systems described below. Additionally, such P-PII gene sequences can be used to detect P-PII gene regulatory (e.g., promoter or promotor/enhancer) defects which can affect plant growth.

A cDNA of a mutant P-PII gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in a plant species putatively carrying the mutant P-PII allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant P-PII allele to that of the normal P-PII allele, the mutation(s) responsible for the loss or alteration of function of the mutant P-PII gene product can be ascertained.

Alternatively, a genomic library can be constructed using DNA obtained from a plant species suspected of or known to carry the mutant P-PII allele, or a cDNA library can be constructed using RNA from a tissue known, or suspected, to express the mutant P-PII allele. The normal P-PII gene or any suitable fragment thereof may then be labeled and used as a probe to identify the corresponding mutant P-PII allele in such libraries. Clones containing the mutant P-PII gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant P-PII allele in a plant species suspected or known to carry such a mutant allele. In this manner, gene products made by the putatively mutant tissue may be expressed and screened using standard antibody screening techniques in conjunction with antibodies raised against the normal P-PII gene product, as described, below, in Section 5.3. (For screening techniques, see, for example, Harlow, E. and Lane, eds., 1988, "Antibodies: A Laboratory Manual", Cold Spring Harbor Press, Cold Spring Harbor.) Additionally, screening can be accomplished by screening the labeled P-PII fusion proteins. In cased where a P-PII mutation results in an expressed gene product with altered function (e.g., as a result of a missense or a frameshift mutation), a polyclonal set of antibodies to P-PII are likely to cross-react with the mutant P-PII gene product. Library clones detected via there reaction with such labeled antibodies can be purified and subjected to sequence analysis according to methods well known to those of skill in the art.

The invention also encompasses nucleotide sequences that encode mutant P-PII, peptide fragments of the P-PII, truncated P-PII, and P-PII fusion proteins. These include, but are not limited to nucleotide sequences endocing mutant P-PII described infra.

Due to the degeneracy of the nucleotide coding sequences, other DNA sequences which encode substantially the same amino acid sequences as depicted in FIG. 1 may be used in the practice of the present invention for the cloning and expression of P-PII. Such alterations include deletions, additions or substitutions of different nucleotide residues resulting in a sequence that encodes the same or functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

The genomic sequences for P-PII may be obtained from any plant cell source, whereas mRNA for preparation of cDNA copies may be obtained from cell sources that produce P-PII. For example, parts of plants (e.g., leaves, stems, roots, nodules, cotyledons, seeds, fruits, etc.) may be ground and used as the source for extracting DNA or RNA. Preferably, the RNA is isolated from shoots, roots or flowers after exposure to light or treatment with sucrose. Alternatively, plant cell lines can be used as a convenient source of DNA or RNA. Genetically engineered microorganisms or cell lines containing P-PII coding sequences, such as the deposited embodiments described herein, may be used as a convenient source of DNA for this purpose.

The P-PII coding sequence may be obtained by cDNA cloning of RNA isolated and purified from such cellular sources or by genomic cloning. Either cDNA or genomic libraries may be prepared from the DNA fragments 'generated using techniques well known in the art, including but not limited to the use of restriction enzymes. The fragments which encode P-PII may be identified by screening such libraries with a nucleotide probe that is substantially complementary to any portion of the nucleotide sequences depicted in FIGS. 12 and 13. Although portions of the coding sequence may be utilized, full length clones, i.e., those containing the entire coding region for P-PII, may be preferable for expression. To these ends, techniques well known to those skilled in the art for the isolation of DNA, generation of appropriate restriction fragments, construction of clones and libraries, and screening recombinants may be used. For a review of such techniques see, for example, Sambrook et al., 1989, Molecular Cloning A Laboratory Manual 2nd. ed., Cold Spring Harbor Press, N.Y. Alternatively, oligonucleotides derived from P-PII sequences could be used as heterologous primers in PCR (polymerase chain reactions),to generate cDNA or genomic copies of P-PII sequences from other species. For a review of such PCR techniques, see for example, Gelfand, D. H., 1989, "PCR Technology. Principles and Applications for DNA Amplification," Ed., H. A. Erlich, Stockton Press, N.Y.; and "Current-Protocols in Molecular Biology," Vol. 2, Ch. 15, Eds. Ausubel et al., John Wiley & Sons, 1988.

In an alternate embodiment of the invention, the coding sequences of FIGS. 12 and 13 could be synthesized in whole or in part, using chemical methods well known in the art. See, for example, Caruthers, et al., 1980, Nuc. Acids Res. Symp. Ser. 7:215–233; Crea and Horn, 180, Nuc. Acids Res. 9(10): 2331; Matteucci and Caruthers, 1980, Tetrahedron Letters 21:719; and Chow and Kempe, 1581, Nuc. Acids. Res. 9(12) 2807–2817. Alternatively, the protein itself could be produced using chemical methods to synthesize the amino acid sequences depicted in FIGS. 12 and 13 in whole or in part. For example, peptides can be synthesized by solid phase techniques, cleaved from the resin, and purified by preparative high performance liquid chromatography. (E.g., see, Creighton, 1983, Proteins Structures And Molecular Principles, W. H. Freeman and Co., N.Y. pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49).

In the specific embodiments described in the examples herein, the *Arabidopsis* P-PII coding sequence was obtained by direct cloning of genomic sequences using a heterologous P-PII cDNA probe from Ricinus. The P-PII genomic sequence was used in turn to obtain an *Arabidopsis* P-PII cDNA clone. Homology between P-PII and bacterial PII was determined to be approximately 37% to 50%, suggesting that bacterial PII and (P-PII) are evolutionarily related, yet quite distinct molecules (FIG. 1). Southern blot analysis of *Arabidopsis* nuclear DNA revealed that P-PII is encoded by a single or low-copy number gene (FIG. 2). Northern blot analysis of *Arabidopsis* RNA revealed that the P-PII is expressed in shoots, roots and flowers (FIG. 3). Our analysis of P-PII mRNA has shown that P-PII mRNA accumulates in these organs after induction by light or sucrose (FIGS. 4 and 5, respectively).

5.2. Expression of P-PII Protein

The invention also encompasses (a) DNA vectors that contain any of the foregoing P-PII coding sequences and/or their complements (i.e., antisense); (b) DNA expression vectors that contain any of the foregoing P-PII coding sequences operatively associated with a regulatory element that directs the expression of the coding sequences; and (c) genetically engineered host cells that contain any of the foregoing P-PII coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the promoters derived from the genome of plant cells (e.g., heat shock promoters; the promoter for the small subunit of RUBISCO; the promoter for the chlorophyll a/b binding protein) or from plant viruses (e.g., the 355 RNa promoter of CaMV; the coat protein promoter of tobacco mosaic virus (TMV), cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

In order to express a biologically active P-PII, the nucleotide sequence coding for P-PII, or a functional equivalent as described in Section 5.1 supra, is inserted into an appropriate expression vector, i.e., a vector which contains the necessary elements for the transcription and translation of the inserted coding sequence. The P-PII gene product as well as host cells, cell lines or plants transfected or transformed with recombinant P-PII expression vectors can be used for a variety of purposes. These include but are not limited to generating antibodies (i.e. monoclonal or polyclonal) that define P-PII; creating mutant P-PII proteins which are constitutively active; creating transgenic plants containing such constitutively active mutant P-PII genes; (creating mutant P-PII proteins which are resistant to herbicides; creating transgenic plants containing such herbicide resistant mutant P-PII genes); or creating transgenic plants which over-express P-PII and demonstrate herbicide resistance; screening and selecting for P-PII inhibitors or activators which may be used as herbicides.

5.3. Construction of Expression Vectors Containing the P-PII Coding Sequence Methods which are well known to those skilled in the art can be used to construct expression vectors containing the P-PII coding sequence and appropriate transcriptional/translational control signals. These methods include in vitro recombinant DNA techniques, synthetic techniques and in vivo recombination/genetic recombination. See, for example, the techniques described in Sambrook et al., 1989, Molecular Cloning A Laboratory Manual, 2nd ed., Cold Spring Harbor Laboratory, N.Y.).

A variety of host-expression vector systems may be utilized to express the P-PII coding sequence. These include but are not limited to microorganisms such as bacteria transformed with recombinant bacteriophage DNA, plasmid DNA or cosmid DNA expression vectors containing the P-PII coding sequence; yeast transformed with recombinant yeast expression vectors containing the P-PII coding sequence; insect cell systems infected with recombinant virus expression vectors (e.g., *baculovirus*) containing the P-PII coding sequence; plant cell systems infected with recombinant virus expression vectors (e.g., cauliflower mosaic virus, CAMV; tobacco mosaic virus, TMV) or transformed with recombinant plasmid expression vectors (e.g., Ti plasmid) containing the P-PII coding sequence; or animal cell systems infected with recombinant virus expression vectors (e.g., adenovirus, vaccinia virus) containing the P-PII coding sequence.

The expression elements of these vectors vary in their strength and specificities. Depending on the host/vector system utilized, any of a number of suitable transcription and translation elements, including constitutive and inducible promoters, may be used in the expression vector. For example, when cloning in bacterial systems, inducible promoters such as pi of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells heat shock promoters; the promoter for the small subunit of RUBISCO; the promoter for the chlorophyll a/b binding protein) or from plant viruses (e.g., the 35S RNA promoter of CAMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used. Promoters produced by recombinant DNA or synthetic techniques may also be used to provide for transcription of the inserted P-PII coding sequence.

In bacterial systems a number of expression vectors may be advantageously selected depending upon the use intended for the P-PII expressed. For example, when large quantities of P-PII are to be produced for the generation of P-PII antibodies, vectors which direct the expression of high levels of fusion protein products that are readily purified may be desirable. Such vectors include but are not limited to the *E. coli* expression vector pUR278 (Ruther et al., 1983, EMBO J. 2:1791), in which the P-PII coding sequence may be ligated into the vector in frame with the lac Z coding region so that a hybrid P-PII-lac Z protein is produced; pIN vectors (Inouye & Inouye, 1985, Nucleic acids Res. 13:3101–3109; Van Heeke & Schuster, 1989, J. Biol. Chem. 264:5503–5509),; and the like. However, where the P-PII expression vector is to be used in an Asn-gln B-host for complementation assays described infra, the expression of unfused P-PII using expression vectors with few or no host genotype requirements, including, but not limited to vectors such as ptac12, (Amann et al., 1983, Gene 25:167) and the like may be preferred.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch-13; Grant et al., 1987, Expression and Secretion Vectors for Yeast, in Methods in Enzymology, Eds. Wu & Grossman, 31987, Acad. Press, N.Y., Vol. 153, pp.516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II. For complementation assays in yeast, pea cDNAs for P-PII may be cloned into yeast episomal plasmids (YEp) which replicate autonomously in yeast due to the presence of the yeast $2\mu$ circle. The P-PII sequence may be cloned behind either a constitutive yeast promoter such as ADH or LEU2 or an inducible promoter such as GAL (Cloning in Yeast, Chpt. 3, R. Rothstein In: DNA Cloning Vol.11, A Practical Approach, Ed. D M Glover, 1986, IRL Press, Wash., D.C.). Constructs may contain the 5' and 3' non-translated regions of the cognate plant mRNA or those corresponding to a yeast gene. YEp plasmids transform at high efficiency and the plasmids are extremely stable. Alternatively vectors may be used which promote integration of foreign DNA sequences into the yeast chromosome.

In cases where plant expression vectors are used, the expression of the P-PII coding.sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

An alternative expression system which could be used to express P-PII is an insect system. In one such system, *Autographa californica* nuclear polyhedrosis virus (AcNPV) is used as a vector to express foreign genes. The virus grows in *Spodoptera frugiperda* cells. The P-PII coding sequence may be cloned into non-essential regions (for example the polyhedrin gene) of the virus and placed under control of an AcNPV promoter (for example the polyhedrin promoter). Successful insertion of the P-PII coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Viol. 46:584; Smith, U.S. Pat. No. 4,215,051).

In cases where an adenovirus is used as an expression vector, the P-PII coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing P-PII in infected hosts. (E.g., See Logan & Shenk, 1984, Proc. Natl. Acad. Sci. (USA) 81:3655–3659). Alternatively, the vaccinia 7.5K promoter may be used. (E.g., see Mackett et al., 1982, Proc. Natl. Acad. Sci. (USA) 79:7415–7419; Mackett et al., 1984, J. Virol. 49:857–864; Panicali et al., 1982, Proc. Natl. Acad. Sci. 79:4927–4931).

Specific initiation signals may also be required for efficient translation of inserted P-PII coding sequences. These signals include the ATG initiation codon and adjacent sequences. In cases where the entire P-PII gene, including its own initiation codon and adjacent sequences, are inserted into the appropriate expression vectors, no additional translational control signals may be needed. However, in cases where only a portion of the P-PII coding sequence is inserted, exogenous translational control signals, including the ATG initiation codon, must be provided. Furthermore, the initiation codon, must be in phase with the reading frame of the P-PII coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153:516–544).

In addition, a host cell strain may be chosen which modulates the expression of the inserted sequences, or modifies and processes the gene product in the specific fashion desired. Expression driven by certain promoters can be elevated in the presence of certain inducers, (e.g., zinc and cadmium ions for metallothionein promoters). Therefore, expression of the genetically engineered P-PII may be controlled. This is important if the protein product of the cloned foreign gene is lethal to host cells. Furthermore, modifications glycosylation) and processing (e.g., cleavage) of protein products may be important for the function of the protein. Different host cells have characteristic and specific mechanisms for the post translational processing and modification of proteins. Appropriate cells lines or host systems can be chosen to ensure the correct modification and processing of the foreign protein expressed.

One way to select for the expression of a biologically active P-PII gene product, be it wild type, mutated or altered, and/or to screen for new herbicides, is to introduce an appropriate expression vector containing the P-PII coding sequence into PII-minus strains of bacteria. The ability of an P-PII cDNA to complement the host cells, indicates the expression and formation of an active P-PII protein. A number of different PII-minus strains may be used for this purpose including but not limited to *E. coli, Klebsiella pneumoniae* and *Synechococeus* name but a few. Heterologous host systems may require the use of a second selectable marker as a means for selecting incorporation of the vector., e.g., in cases where P-PII may not complement the PII-minus phenotype. To this end, dominant selectable markers such as antibiotic-resistance genes may be used.

5.4. Identification of Transfectants or Transformants Expressing the P-PII Gene Product and Isolation of P-PII The host cells which contain the P-PII coding sequence and which express the biologically active P-PII gene product may be identified by these general approaches: (a) DNA-DNA hybridization; (b) the presence or absence of "marker" gene functions; (c) assessing the level of transcription as measured by the expression of P-PII mRNA transcripts in the host cell; and (d) detection of the P-PII gene product as measured by immunoassay or by its biological activity; or (e) phenotypic rescue.

In the first approach, the presence of the P-PII coding sequence inserted in the expression vector can be detected by DNA-DNA hybridization using probes comprising nucleotide sequences that are homologous to the P-PII coding sequences substantially as shown in FIGS. 12 and 13 or portions or derivatives thereof.

In the second approach, the recombinant expression vector/host system can be identified and selected based upon the presence or absence of certain "marker" gene functions (e.g., resistance to antibiotics, resistance to methotrexate, transformation phenotype, occlusion body formation in baculovirus, etc.). For example, if the P-PII coding sequence is inserted within a marker gene sequence of the vector, recombinants containing the P-PII coding sequence can be identified by the absence of the marker gene function. Alternatively, a marker gene can be placed in tandem with the P-PII sequence under the control of the same or different promoter used to control the expression of the P-PII coding sequence. Expression of the marker in response to induction or selection indicates expression of the P-PII coding sequence. Two marker gene constructs which may be of particular-value for monitoring promoter activity in plant cells and plants are the bacterial glucuronidase gene, GUS (Jefferson et al., 1987, EMBO J. 6:3901–3908) or the luciferase gene (Ow et al., 1987, Science, 234:856–859).

In the third approach, transcriptional activity for the P-PII coding region can be assessed by hybridization assays. For example, RNA can be isolated and analyzed by Northern blot using a probe homologous to the P-PII coding sequence or particular portions thereof substantially as shown in FIGS. 12 and 13. Alternatively, total nucleic acids of the host cell may be extracted and assayed for hybridization to such probes.

In the fourth approach, the expression of the P-PII protein product can be assessed immunologically, for example by Western blots immunoassays such as radioimmuno-precipitation, enzyme-linked immunoassays and the like.

In the fifth approach, the production of a biologically active P-PII gene product can be assessed by the complementation assay, in which an PII-minus bacterial transformed or transfected with the P-PII expression vector will rescue the mutant phenotype. As previously explained, this may be used in conjunction with a separate selectable marker to ensure incorporation of the vector.

In the sixth approach, mutant P-PII which is constitutively active can be selected using the complementation assay expression system by exposing the clones which express mutant P-PII to various concentrations of sucrose.

Once a clone that produces high levels of biologically active P-PII is identified, the clone may be expanded and used for a variety of ends; e.g., production of P-PII which may be purified using techniques well known in the art including but not limited to immunoaffinity purification, chromatographic methods including high performance liquid chromatography, and the like; screening herbicides; and engineering transgenic plants which have high nitrogen assimilatory efficiency.

5.5. Uses of P-PII Gene and Gene Product

Our studies concerning P-PII mRNA accumulation have highlighted the importance of the P-PII mRNAs in plant nitrogen metabolism. The P-PII cDNA clones can be used to characterize the P-PII gene product; to express P-PII so that antibodies which define P-PII gene product can be produced; to screen and develop new herbicides; to develop herbicide resistant plants, nitrogen efficient plants.

5.6. Production of Antibodies that Define P-PII

Expressed gene products may be used to produce antibodies that define P-PII. These antibodies can be used in fractionation studies to define the cellular and tissue site of action of P-PII polypeptide. For full length cDNA clones, the corresponding proteins may be produced in *E. coli* in sufficient quantities to allow characterization in terms of substrate preference (i.e. sucrose and other sugars), Km, sensitivity to inhibitors, etc.

Such antibodies may be produced by any method known in the art, including, but not limited to injection of P-PII into mice, rats, rabbits, or other host species for production of polyclonal antisera. Various adjuvants may be used to increase the immune response. These include, but are not limited to Freund's (complete and incomplete), mineral gels such as aluminum hydroxide, surface active substances such as lysolecithin, pluronic polyols, polyanions, peptides, and oil emulsions. For a review of such techniques, see Harlow & Lane, 1988, Antibodies A Laboratory Manual, Cold Spring Harbor Laboratory.

Monoclonal antibodies, or fragments thereof, can be prepared by any technique which provides for the production of antibody molecules by continuous cell lines in culture. Such techniques include but are not limited to the hybridoma technique first developed by Kohler and Millstein (1975, Nature 256:495–497), the human B-cell hybridoma technique (Kozbor et al., 1983, Immunology Today 4:72), and the EBV-hybridoma technique for production of human monoclonal antibodies (Cole et al., 1985, Monoclonal Antibodies and Cancer Therapy, Alan R. Liss, Inc., pp. 77–96).

Antibody fragments which contain the idiotype of the molecule could be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the 2 Fab or Fab fragments which can be generated by treating the antibody molecule with pepsin and a reducing agent.

5.7. Development of New Herbicides

P-PII cDNA clones can be used in functional complementation assays described in Section 5.1, supra, designed to screen for new herbicides as follows. Full length P-PII cDNAs cloned in the appropriate expression vectors can be introduced into PII-minus strains of bacteria as previously described. The ability of a P-PII cDNA clone to rescue the PII-minus mutant cells would indicate that the cDNA encodes an P-PII polypeptide which is active in these heterologous environments.

The P-PII cDNAs expressed in PII-minus mutants of bacteria described previously provide an in vivo system to select for herbicides which selectively act on P-PII. To this end, known concentrations of a test substance can be added to the growth media in order to select those substances which inhibit cell growth as an indication of P-PII inhibitory activity.

5.8. Development of Herbicide Resistant Plants and Nitrogen-Efficient Plants The in vivo expression system described above could be modified and used to select for mutations in the P-PII structural gene which are constitutively active or confer growth resistance to the new herbicides. Mutations may be introduced into the P-PII cDNA in vivo or in vitro using techniques well known in the art, including, but not limited to, radiation, chemical mutation, site-specific mutations, etc. For example, see Tilghman and Levine, 1987, in Gene Transfer, Kucherlaputi, Ed., Plenum Pub., N.Y., pp. 189–221). Expression vectors containing such altered or mutated P-PII coding sequences can be used in PII-minus bacterial hosts in the complementation assay described above to identify clones containing coding sequences that specify and express biologically active, altered P-PII. Clones which produce constitutively active or herbicide resistant P-PII can be selected by growth in the absent of inducer or the presence of the herbicide, respectively. In this way, clones which produce mutant P-PII can be screened for constitutive activity or resistance to new herbicides.

Plants may then be engineered for enhanced nitrogen utilizations or resistance to herbicides using appropriate constructs containing the mutated P-PII genes which overexpress wild-type P-II or antisense to P-PII which results in down regulation of P-PII expression. In either case, such transgenic plants may be constructed using methods well known to those skilled in the art including but not limited to techniques involving the use of the Ti plasmids (eg., *Agrobacterium rhizogenes*), plant viruses, electroporation, direct transformation, microinjection, etc. By way of example, and not by way of limitation, the binary Ti vector system could readily be used to this end (Bevan, 1984, Nuc. Acids Res. 12:8711–8721). This vector contains a selectable marker, neomycin phosphotransferase (kanR), under direction of the nopaline synthetase promoter (nos) for KanR selection in plants, and unique cloning sites for EcoRI, HindIII, BamHI, SmaI, SalI, KpnI, baI, SstI. Using this system, DNA fragments cloned into one of the unique cloning sites located between the left and right T-DNA borders are transferred into dicot plants when introduced into *Agrobacterium tumefaciens* LB4404 or GU3010 harboring a resident disarmed Ti plasmid which will provide vir gene required for T-DNA transfer in trans. Another vector system which could be used is the pMON505 intermediate binary Ti transformation vector (Horsch & Klee, 1986, Proc. Natl. Acad. Sci. 83, 4428–4432; Horsch et al., 1985 Science, 227:1229–1231). For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9. P-PII genes altered in vivo or in vitro to overproduce wild type P-PII or constitutively active or herbicide resistant forms of P-PII enzymes may be used as dominant selectable markers for transformation systems which include organisms such as bacteria, algae, yeast, neurospora and plants.

By way of illustration, enhanced nitrogen utilization or herbicide resistant plants can be engineered in at least two ways: P-PII cDNAs which contain mutations conferring constitutive activity or herbicide resistance as measured in the screening assay above, can be introduced into transgenic plants under the transcriptional regulation of a strong constitutive promoter (e.g., 35S promoter of CaMV) or an inducible promoter (.eg., the promoter of the small subunit of RUBISCO; a heat shock promoter, etc.). Mutant P-PII produced in the transgenic plants will confer enhanced nitrogen utilization or herbicide resistance. Alternatively, enhanced nitrogen utilization or herbicide resistant plants could be developed by the over-expression or underexpression of the wild-type P-PII cDNA. The overexpression or antisense of P-PII in these transgenic plants will produce plants with enhanced nitrogen utilization properties or resistant to high levels of a herbicide specific of P-PII.

5.9. THE P-PII Promoter

As described above and exemplified below, the P-PII promoter directs expression in shoots, roots and flowers. This promoter can be used to direct the regulated expression of heterologous gene sequences in appropriate hosts. The P-PII promoter described herein is not only inducible by light or sucrose, but drives high levels of transcription in flowers.

The P-PII promoter may be isolated from the P-PII genomic clones.

The organ-specific and photo inducible P-PII promoter can be used in a variety of DNA vectors to drive the expression of heterologous sequences ligated after the transcription start site. Heterologous sequences ligated downstream of the transcription start site, containing a portion of the leader sequence, will require translational control elements such as the ATG start signal, and ribosome binding sites etc. optionally, the heterologous sequences may also be ligated in a translational fusion to marker genes such β-galactosidase, GUS, luciferase, etc. to produce fusion proteins.

Such expression vectors may be used in plant cell culture or in transgenic plants to direct high level expression of the heterologous sequence in an inducible, temporal, or organ-specific fashion.

6. EXAMPLE

Arabidopsis and Castor Bean P-PII Gene

A plant gene GLB1 encoding a PII homologue was identified, the first time a PII gene has been identified in a eukaryote. This plant PII-homologue was identified as a cDNA present in an Expressed Sequence Tag (EST) library of castor (*Ricinus communes*) (van de Loo et al., 1995, Plant Physiol.) and was subsequently cloned from *Arabidopsis*. In this example, the two plant GLB1 cDNAs encoding PII are characterized and it is shown that their deduced protein sequences have striking identity to microbial PII. It is also demonstrated that the regulation of GLB1 mRNA levels by light and by metabolites correlates with the activation of putative downstream genes such as chloroplastic GS2 (GLN2) (Faure et al., 1994, *Plant J.* 5:481–491; Edwards, J. W. and Coruzzi, G. M., 1989, Plant Cell 1:241–248). Combined with previous findings that plant nitrogen assimilatory genes are regulated by carbon and nitrogen metabolites (Faure et al., 1994, *Plant J.* 5:481–491; Lam et al., 1994, Plant Physiol. 106:1347–1357; Vincentz et al., 1993, Plant J. 3:315–324), these results suggest that PII may be the first nitrogen regulatory protein identified in plants controlling the assimilation of inorganic nitrogen into organic form. As nitrogen assimilation into organic form may be a critical rate-limiting element in plant growth, the discovery of a gene that regulates this process may have important implications to improving nitrogen-use efficiency in plants.

Materials and Methods

Plant Materials

The plant tissues used in all experiments were from *Arabidopsis thaliana* Columbia ecotype. Plants used for genomic DNA extraction, RNA isolation from different organs were grown in soil. Others were grown in a semi-hydroponic system developed by Applicants (I. Oliveira and G. Coruzzi, unpublished). This system contains MS salt mixture (Sigma) plus 0.4% agar in Plantcons (ICN Laboratories Inc.). *Arabidopsis* seeds were sown on Nylon grids (250 $\mu$M) (Tetko Inc.) placed on the surface of the media. Plants were grown in EGC growth chambers at 45 $\mu$E m$^{-2}$ sec$^{-1}$ on a 16 h light/8 h dark cycle, unless otherwise noted.

Isolation of Castor and Arabidopsis GLB1 cDNA Clones

A λZAPII library containing cDNAs from developing endosperm and embryos of castor (*Ricinus communis* L.) seeds was used for mass-sequencing (van de Loo et al., 1995, Plant Physiol.). Out of 743 clones sequenced, one clone showed sequence similarity to nitrogen-regulatory protein PII of *Synechococcus* and other bacteria (Tsinoremas et al., 1991, Proc. Natl. Acad. Sci. USA 88:4565–4569). This 0.85 kb cDNA called pRc-GLB1 was used to make a $^{32}$P-dCTP labeled probe by random priming and used to screen an *Arabidopsis* genomic library at a reduced stringency as follows. The hybridization was performed in QuickHyb (Stratagene) at 50° C. for 1 hr. Filters were washed with 2xSSC, 0.1% SDS, 5 mm twice at room temperature followed by 0.5xSSC, 0.1% SDS wash at 50° C. for 30 mm. One *Arabidopsis* genomic GLB1 clone with a 3 kb DNA insert was isolated. A 1.1 kb NcoI-NcoI DNA fragment of the genomic clone which strongly hybridized to the castor GLB1 cDNA was used to screen an *Arabidopsis silique* cDNA library. Under high-stringency hybridization conditions, two Arabidopsis cDNA clones were obtained from 2x10$^5$ plaques. These *Arabidopsis* GLB1 cDNAs were sequenced using the Sequenase method (U.S. Biochemical Corp.). DNA sequences were analyzed by the GCG Sequence Analysis software package (Genetics Computer Group Inc., Madison, Wis.). 5' RACE was performed using Gibco-BRL 5' RAGE system. Reverse transcription was performed with 1 $\mu$g total RNA from light-grown plants. Nested primers for RACE were MH7 (GCAAGATGGTCGGGAATGTC) (SEQ ID NO:17), MH8 (CGACAGGTAAAACACGACTG) (SEQ ID NO:18) and MH9 (GGTCTGACAATTGCTTCCAC) (SEQ ID NO:19). PCR conditions were 94° C. 2 mm, followed by 30 cycles (94° C. 20 sec, 55° C. 30 sec, and 72° C. 40 sec). PCR products were subcloned using the pCR-Script kit of Stratagene.

Analyses of DNA and RNA

*Arabidopsis* genomic DNA was isolated according to the procedure described by Ausubel et. al, 1987, In: Current Protocols in Molecular Biology, (Greene Publishing Assoc. & John Wiley & Son), except that the buffer used was 8.75 M urea, 438 mM NaCl, 62.5 mM Tris-HCl pH 8.0, 62.5 mM EDTA. RNA was isolated using a phenol extraction protocol (Jackson, A. O. and Larkins, B. A., 1976, Plant Physiol. 57:5–10). Southern blot and Northern blot were performed as described (Sanibrook et al., Molecular cloning: a laboratory manual, 3rd ed. (Cold Spring Harbor Laboratory, Cold Spring Harbor Laboratory)). For detection of GLB1 mRNA, membranes were hybridized with single-stranded DIG-labeled probes made from pAt-GLB1 cDNA using PCR (Myerson, D., 1991, Biotechniques 10:35–38). To generate probes approximately 540 nucleotides in length covering the PII coding region and partial 3' non-coding region, MH5 (GAAACCAAACACAGACTCC) (SEQ ID NO:20) and MH6 (CCGAGTAATAACAGTCGTC) (SEQ ID NO:21) primers were used. The control DIG-labeled probes for GLN2, P-PIIN1 and 18 rRNA were made by random priming (Boehinger Mannheim).

Computer Analysis

Geneworks (Intelligenetics Inc) was used to align the polypeptide sequences of plant and bacterial PIIs. Phylogenetic analysis was performed using the heuristic option of PAUP 3.1.1 (phylogenetic analysis using parsimony) (Stewart, C-B., 1993, Nature 361:603–607). Archaebacterial PII-like protein 1 was selected as the outgroup. To generate the appropriate alignment for use in PAUP, insertions and deletions were introduced using 'MALIGNED' (Clark, S. P., 1992, Comput. Appl. Biosci. 8:535–538). The PII sequences for bacteria and archaebacteria were obtained from Gen-Bank.

Results

Cloning and Identification of *Arabidopsis* and Castor PII-homologue cDNAs

By mass-sequencing of portions of cDNAs from a castor developing seed library, a 0.85 kb cDNA clone, pCRS852, was identified which showed significant similarity to the nitrogen-regulatory protein PII of enteric bacteria encoded by glnB. This plant cDNA clone was named pRc-GLB1 and was further analyzed and the sequence of the entire clone determined. The castor glnB-like cDNA was used to isolate an *Arabidopsis* cDNA homologue. Two independent *Arabi-*

*dopsis* clones with same size cDNA insert, 0.82 kb, were obtained. The nucleotide sequence of these two *Arabidopsis* cDNA clones encoding P-PII revealed that they possess identical sequences in the coding region and non-coding regions. One clone extends further at the 3' end and appears to use a different polyadenylation site (data not shown). Thus, these two *Arabidopsis* cDNAs were considered to be derived from the same GLB1 gene. These *Arabidopsis* cDNAs encoding P-PII are judged to be full-length for the following reasons. First, the size of the cDNA is consistent with that predicted for the mRNA based on Northern blot analysis. Second, three independent 5'-RACE products all showed an in-frame TAA stop codon 45 nucleotides upstream of the first ATG (data not shown).

The *Arabidopsis* PII (GLB1) gene maps to the top arm of chromosome 4. RFLP and recombinant inbred lines of *Arabidopsis* were used to map the PII (GLB1) gene to the top arm of chromosome 4 at position 10.8 (FIG. 10).

Plant PII has Significant Similarity to Microbial PII Proteins.

The P-PII polypeptide encoded by the *Arabidopsis* GLB1 cDNA is 196 amino acids long with a molecular weight of 22 kD daltons. The region of homology to bacterial PII occurs between amino acids 74 and 186 of the *Arabidopsis* P-PII protein. This region encompasses the entire microbial PII protein (FIG. 1A). In this region, the overall identity between plant and *E. coli* PII is 50.9%. The identity between P-PII and *E. coli* PII is extremely high in two "signature domains" (Son, H. S. and Rhee, S. G., 1987, J. Biol. Chem. 262:8690–8695) conserved amongst all PII proteins (85%) (FIG. 1A). Within the region corresponding to *E. coli* PII (residues 74–186 of Arabidopsis P-PII) the two plant cDNAs are 90.3% identical (FIG. 1A). Beyond this region, the identity between these two P-PII proteins decreases to 32.9% at the amino termini and 40% at the carboxy-termini (data not shown). When the deduced P-PII amino acid sequences are compared with those of microbial glnB genes encoding PII, high overall identities are found with *E. coli* (50.9%) (Son, H. S. and Rhee, S. G., 1987, J. Biol. Chem. 262:8690–8695), *Synechococcus* sp. PCC 7942 (56.4%) (Tsinoremas et al., 1991, Proc. Natl. Acad. Sci. USA 88:4565–4569), *Klebsiella pneumoniae* (50.9%) (Holtel, A. and Merrick, M., 1988, Mol. Gen. Genet. 215:134–138), *Azospirillum brasilense* (49.1%) (de Zamaroczy et al., 1990, Mol. Gen. Genet. 224:421–430), *Rhodobacter capsulatus* (48.2%) (Kranz et al. 1990, J. Bacteriol. 172:53–62. *Rhizobium leguminosarum* (47.7%) Colonna-Romano et al., 1987, Nucleic Acids Res. 15:1951–1964, *Bradyrhizobium japonium* (47.7%) (Martin et al., 1989, J. Bacteriol. 171:5638–5645), *Bacillus subtilis* (38.6%) (Wray et al., 1994, J. Bacteriol. 176:108–114) and with *Methanococcus thermolithotrophicus* (archaebacteria) glnB-like protein 1 (34.9%) (Souillard, N. and Sibold, L., 1989, Mol. Microbiol. 3:541–551).

In addition to the high overall identity amongst various PII proteins of bacteria and plants, the P-PII proteins share extremely high regional identities over signature domains 1 and 2 (85%). Signature domain 1 contains the Tyr 51 residue which is post-translationally modified by uridylylation in enteric bacteria (Magasanik, B., 1988, TIBS 13:475–479). As the glnB mRNA is constitutively expressed in *E. coli* (van Heeswijk et al., 1993, Mol. Microbiol. 9:443–457). The activity of the PII protein product is regulated post-translationally by uridylylation. Although the uridylylation of Tyr51 is considered an important feature of signature domain 1 of bacterial PII proteins, exceptions do exist. In Bacillus, the PII-like protein does not contain this conserved tyrosine residue. However it is not known if this is a functional PII protein (Wray et al., 1994, J. Bacteriol. 176:108–114). In cyanobacteria, although PII possesses Tyr 51, its activity is regulated by phosphorylation at a serine residue (Forchhammer, K. and De Marsac, N. T., 1994, J. Bacteriol. 176:84–91). In both plant PII proteins, the Tyr 51 is replaced by a phenylalanine (FIG. 1). Interestingly, there is only one nucleotide change between tyrosine and phenylalanine codons. The lack of Tyr 51 in the P-PII proteins suggests that the P-PII protein may not be regulated post-translationally by uridylylation. The conserved signature domain-2 common to all bacterial PIIs, is extremely well conserved with *Arabidopsis* and castor PII proteins (FIG. 1A). The extremely high conservation between prokaryotic and eukaryotic PII suggests that this second domain plays an important, but as yet unknown role in PII function.

A phylogenetic analysis of the evolutionary relationship among different PII proteins in plants and bacteria was performed using a parsimony method(PAUP) (Stewart, C-B., 1993, Nature 361:603–607). (FIG. 1B). Archaebacteria was used as the outgroup in this tree. The overall homology between plant PII protein and bacterial PII (50%) is significantly higher than plant PII is to the archaebacteria (35%). However, the Tyr51 residue, which is conserved in the PII proteins of cyanobacteria and most of the eubacteria, is replaced by a Phe in both plants and archaebacteria.

GLB1 Encoding a PII Homologue is a Single- or Low-Copy Number Gene in *Arabidopsis*.

*Arabidopsis* genomic DNA was digested with several different restriction enzymes and probed with a DNA fragment from the GLB1 cDNA (FIG. 2). In each lane, one or several *Arabidopsis* genomic DNA fragments hybridized to the GLB1 cDNA clone. Preliminary restriction enzyme analysis of an *Arabidopsis* GLB1 genomic clone encoding PII was also performed. These data indicate that PII is truly encoded by a plant gene, GLB1, and that in *Arabidopsis* is a single- or low-copy number gene.

7. EXAMPLE

Induction of PII mRNA in Response to Light and Sucrose

These studies demonstrate that P-PII mRNA is expressed in both photosynthetic and non-green Arabidopsis organs and that the expression of the P-PII gene is induced by light and sucrose.

7.1. The GLB1mRNA Encoding PII is Expressed in Photosynthetic and Non-Green *Arabidopsis* Organs The expression of GLB1 mRNA in different organs of *Arabidopsis* was examined by Northern blot analysis. *Arabidopsis* GLB1 mRNA is detected in shoots, roots, and flowers (FIG. 3 lanes 1–3). The expression of GLB1 mRNA in different organs may reflect the function of the PII protein in each tissue. For example, primary ammonium assimilation via GS/GOGAT occurs primarily in photosynthetic organs. It is therefore reasonable to detect higher levels of GLB1 mRNA in leaves compared to roots (FIG. 3, lanes 1 & 2). The high level expression of GLB1 mRNA in developing flowers (FIG. 3, lane 3) and siliques with developing seeds (not shown) is consistent with the highly active nitrogen metabolism in these organs.

7.2. Arabidopsis GLB1 mRNA Levels are Induced by Light

Light appears to coordinate the expression of nitrogen assimilatory genes such as NR, GLN2, and GLU1 (encoding Fd-GOGAT) with that of photosynthetic genes such as rbcS. It was examined whether light also induced the accumulation of *Arabidopsis* GLB1 mRNA, a putative nitrogen-regulatory gene (FIG. 4A and GLB1 mRNA was shown to accumulate preferentially in light-grown plants compared to plants dark-adapted for 48 hrs (FIG. 4A, lanes 1 & 2). A time-course of light-induction was conducted and the identical Northern blot was probed simultaneously with DNA probes for GLB1 and its putative downstream target gene GLN2 (FIG. 4B). The induction of GLB1 and GLN2 mRNA levels are coordinately induced by light to maximal induced levels (FIG. 4B, lane 4). This finding is consistent with the hypothesis that the PII protein encoded by GLB1 may regulate downstream nitrogen assimilatory genes such as GLN2.

7.3. Levels of *Arabidopsis* GLB1 NMRNA are Induced by Sucrose

Light via phytochrome has been shown to have a direct effect on the expression of genes for nitrogen assimilatory enzymes such as nitrate reductase (Crawford et al., 1986, Proc. Natl. Acad. Sci. USA. 83:8073–8076), glutamine synthetase (McGrath, R. B. and Coruzzi, G. M., 1991, Plant J. 1:275–280), and glutamate synthase, (Sakakibara, H. et al., 1991, J. Biol. Chem. 266:2028–2035). It appears that light-induced changes in carbon metabolites can also affect gene induction, as sucrose has been shown to induce the expression of NR (Vincentz et al., 1993, Plant J. 3:315–324), GLN2 (Faure et al., 1994, *Plant J.* 5:481–491) and GLU1, independent of light. Metabolic gene induction by sucrose links the expression of nitrogen assimilatory genes with the availability of carbon skeletons. As GLE1 mRNA levels are induced by light, we examined whether sucrose could also affect the expression of Arabidopsis GLB1 mRNA. Steady state levels of GLB1 mRNA are low in dark-adapted plants and are induced by light 10-fold (FIG. 5A, compare lanes 1 & 4). The effect of light on levels of GLB1 mRNA can be mimicked by the addition of 3% sucrose (FIG. 5A, lane 2), but not by mannitol, a non-metabolizable carbon source (FIG. 5A, lane 3). The effects of sucrose on the levels of GLE1 mRNA in dark-adapted *Arabidopsis* parallels the accumulation of mRNA for *Arabidopsis* chloroplast GS2 (GLN2) (Faure et al., 1994, *Plant J.* 5:481–491). and Fd-GOGAT genes (GLU1). Interestingly, sucrose can super-induce GLB1 mRNA accumulation beyond light-induced levels (FIG. 5A, lane 5). Again this effect is not obtained with mannitol (FIG. 5A, lane 6). Table 1 details the quantitation of GLB1 mRNA from two separate experiments. As sucrose acts independent of light to induce GLB1 mRNA, these results prove that the GLB1 gene is subjected to metabolic control.

Induction of PII (GLB1) mRNA by light/sucrose mirrors that of the putative downstream target nitrogen assimilatory genes GS2 (GLN2) and Fd-GOGAT (GLU1). PII mRNA is low in dark-adapted plants and is induced by sucrose in the absense of light, but not by mannitol, a non-metabolizable sugar (FIG. 6). Light induces PII mRNA and light plus sucrose super-induces PII mRNA (lane 5). Mannitol cannot superinduce PII mRNA above light levels. Nitrogen assimilatory genes GS2 and Fd-GOGAT GLU1, also show induction by sucrose or light, but are not super-induced by light and sucrose (FIG. 6).

PII induction by light and/or high sucrose, mirrors the induction of downstream nitrogen assimilatory genes for glutamine synthetase (GLN2), Fd-dependent glutamate synthase (Fd-GOGAT, GLU2), and aspartate amminotransferase (ASP2). By contrast, genes for asparagine synthetase (ASN1) and glutamate dehydrogenase are repressed by high sucrose (FIG. 7).

TABLE 1

Fold-induction of GLB1 mRNA levels induced by light and/or sucrose

| Lane | Treatments | Fold-Induction* |
|---|---|---|
| 1. 1.0 | Dark | 0% Sucrose |
| 2. 7.4 | Dark | 3% Sucrose |
| 4. 10.2 | Light | 0% Sucrose |
| 5. 21.8 | Light | 3% Sucrose |

*GLB1 mRNA signals depicted in FIG. 5 plus a replicate experiment were quantified by densitometry. The average fold-induction relative to lane 1, FIG. 5, is listed.

8. EXAMPLE

PII (GLB1) Expression is Repressed by High Organic Nitrogen, Relative to Carbon This study demonstrates that the regulation of PII mirrors the regulation of the putative downstream nitrogen assimilatory gene for glutamine synthetase (GLN2) (FIG. 8). PII and its putative downstream nitrogen assimilatory genes (GLN2, GLU1 and ASP2) are induced by sucrose (FIG. 9, lane 1). Sucrose induction is repressed by the addition of organic nitrogen as asparagine, glutamine and glutamate (FIG. 9). By contrast, ASN1 and GDH1 are induced by these conditions. These results are consistent with a role for PII in the carbon:nitrogen sensing/signalling mechanism leading to changes in the expression of genes involved in nitrogen assimilation.

9. EXAMPLE

Transgenic Tobacco Plants Expressing Antisense PII mRNA

Antisense *Arabidopsis* PII was introduced into tobacco by Agrobacterium-mediated DNA transfer. Shown are four independent trangenic tobacco lines which express high levels of PII antisense RNA (FIG. 11), lines 1, 2, 5 and 10). Phenotypic analysis of plants is ongoing. In addition, both sense and antisense PII *Arabidopsis* transgenic plants have been created in order to test whether the C:N sensing mechanism is perturbed in these transgeinc plants.

Various publications are cited herein, the disclosures of which are incorporated by reference in their entireties.

The present invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

What is claimed is:

1. A substantially pure polypeptide comprising the amino acid sequence depicted in SEQ ID NO:1.

2. A substantially pure polypeptide comprising the amino acid sequence depicted in SEQ ID NO:2.

3. An isolated polypeptide encoded by a nucleic acid molecule which hybridizes to a nucleic acid molecule consisting of a nucleotide sequence that is the complement of SEQ ID NOs: 13, 14, 15, or 16 under highly stringent conditions and is functionally equivalent to a P-PII polypeptide.

4. The polypeptide of any one of claims 1, 2, or 3, which is recombinantly produced.

5. The polypeptide of any one of claims 1, 2, or 3, which is produced by a chemical synthetic method.

6. A fragment of the polypeptide of any one of claims 1, 2, or 3, wherein the fragment is functionally equivalent to said polypeptide.

7. A fusion polypeptide comprising the polypeptide of any one of claims 1, 2 or 3 and a heterologous polypeptide.

8. The fusion polypeptide of claim 7, wherein the heteologous polypeptide is lac Z, β-galactosidase, GUS, or luciferase.

9. The polypeptide of any one of claims 1 or 2, which further comprises one or more conservative amino acid substitutions in an amino acid sequence comprising the polypeptide.

10. The polypeptide of claim 3, which further comprises one or more conservative amino acid substitutions in an amino acid comprising the polypeptide.

* * * * *